United States Patent
Ito et al.

(10) Patent No.: US 9,400,319 B2
(45) Date of Patent: Jul. 26, 2016

(54) MAGNETIC RESONANCE IMAGING APPARATUS AND METHOD FOR MEASURING IRRADIATION MAGNETIC FIELD

(75) Inventors: Kosuke Ito, Tokyo (JP); Masahiro Takizawa, Tokyo (JP); Shinji Kurokawa, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 613 days.

(21) Appl. No.: 13/880,634

(22) PCT Filed: Oct. 13, 2011

(86) PCT No.: PCT/JP2011/073474
§ 371 (c)(1),
(2), (4) Date: Apr. 19, 2013

(87) PCT Pub. No.: WO2012/060192
PCT Pub. Date: May 10, 2012

(65) Prior Publication Data
US 2013/0207653 A1 Aug. 15, 2013

(30) Foreign Application Priority Data

Nov. 5, 2010 (JP) .................................. 2010-248652
Jul. 1, 2011 (JP) .................................. 2011-147311

(51) Int. Cl.
*G01V 3/00* (2006.01)
*G01R 33/56* (2006.01)
*G01R 33/44* (2006.01)
*G01R 33/24* (2006.01)
*A61B 5/055* (2006.01)
*G01R 33/565* (2006.01)

(52) U.S. Cl.
CPC ................ *G01R 33/56* (2013.01); *A61B 5/055* (2013.01); *G01R 33/246* (2013.01); *G01R 33/443* (2013.01); *G01R 33/5659* (2013.01)

(58) Field of Classification Search
CPC ....................................................... G01R 33/443
USPC .................................................. 324/309, 307
See application file for complete search history.

(56) References Cited

U.S. PATENT DOCUMENTS 8,077,955 B2 * 12/2011 Dannels et al. ............... 382/131
8,198,891 B2 *  6/2012 Sacolick et al. .............. 324/307

(Continued)

OTHER PUBLICATIONS

Mar. 19, 2015 European search report in corresponding European patent application No. 11837843.9.

(Continued)

*Primary Examiner* — Louis Arana
(74) *Attorney, Agent, or Firm* — Cooper & Dunham LLP

(57) ABSTRACT

There is provided an MRI apparatus capable of measuring the B1 distribution of an RF transmission coil in a short time with high accuracy. In order to realize this, imaging means of the MRI apparatus includes a B1 distribution measurement sequence that includes an application of a pre-pulse by RF radiation means and a plurality of signal acquisition sequences with different elapsed time (TI) from the pre-pulse. The signal acquisition sequence uses a pulse having a small flip angle as an RF pulse and is executed before the longitudinal relaxation after the pre-pulse ends. Calculation means calculates the B1 distribution of the RF radiation means using image data with different TI acquired in the respective signal acquisition sequences.

15 Claims, 19 Drawing Sheets

(56) References Cited

U.S. PATENT DOCUMENTS

| | | | |
|---|---|---|---|
| 8,258,786 B2 * | 9/2012 | Hennel | 324/307 |
| 8,558,547 B2 * | 10/2013 | Sacolick et al. | 324/318 |
| 8,890,527 B1 * | 11/2014 | Balcom et al. | 324/309 |
| 2015/0042335 A1 * | 2/2015 | Nehrke et al. | 324/309 |

OTHER PUBLICATIONS

J. B. M. Warntjes et al., "Novel Method for Rapid, Simultaneous T1, T2*, and Proton Density Quantification", Magnetic Resonance in Medicine, 2007, pp. 528-537, vol. 57, Wiley-Liss, Inc.

Jung-Jiin Hsu et al., "Rapid Methods for Concurrent Measurement of the RF-Pulse Flip Angle and the Longitudinal Relaxation Time", Magnetic Resonance in Medicine, 2009, pp. 1319-1325, vol. 61, Wiley-Liss, Inc.

S. Akoka et al., "Radiofrequency Map of an NMR Coil by Imaging", Magnetic Resonance Imaging, 1993, pp. 437-441, vol. 11, Pergamon Press Ltd.

European official action dated Mar. 19, 2015 in corresponding European Patent Application No. 11837843.

Eggenschwiler et al. : "Sa2RAGE—A new sequence for rapid 3D B1+—mapping with a wide sensitivity", Proc. of the IMSMRM 2010, p. 2843.

International Search Report in PCT/JP2011/073474.

F. Eggenschwiler et al., "Sa2RAGE—A new sequence for rapid 3D $B1^+$—mapping with a wide sensitivity range", Proc. Intl. Soc. Mag. Reson. Med., 18, 2010.

T. Wade et al., "B1 Correction using Dual Tau Look-Locker (D$r$LL)", Proc. Intl. Soc. Mag. Reson. Med., 17, 2009.

S. Zhao et al., "A novel method for simultaneous 3D mapping of T1, B1 and B0", Proc. Intl. Soc. Mag. Reson. Med., 17, 2009.

S. Chung et al., "Rapid $B_1$ mapping in the presence of $B_0$ variations", Proc. Intl. Soc. Mag. Reson. Med., 17, 2009.

E. Breton et al., Image-Guided Radio-Frequency Gain Calibration for High-Field MRI, Proc. Intl. Soc. Mag. Reson. Med., 18, 2010.

V. L. Yarnykh et al., "Actual Flip Angle Imaging in the Pulsed Steady State", Proc. Intl. Soc. Mag. Reson. Med., 12, 2004.

H-P. Fautz et al., "B1 mapping of coil arrays for parallel transmission", Proc. Intl. Soc. Mag. Reson., 16, 2008.

Charles H. Cunningham et al., "Saturated double-angle method for rapid $B_1$ + mapping", Proc. Intl. Soc. Mag. Reson., 6, 2006.

\* cited by examiner

MAGNETIC RESONANCE IMAGING APPARATUS AND METHOD FOR MEASURING IRRADIATION MAGNETIC FIELD

TECHNICAL FIELD

The present invention relates to a magnetic resonance imaging apparatus (hereinafter, referred to as an MRI apparatus) and in particular, to an MRI apparatus having a function of measuring the distribution of the irradiation magnetic field of a radiation coil that radiates a high-frequency magnetic field to an object.

BACKGROUND ART

The MRI apparatus is an apparatus that measures a nuclear magnetic resonance (NMR) signal, which is generated by applying a high-frequency magnetic field pulse to an object to be tested in a state where the object to be tested is placed in a uniform static magnetic field, and reconstructs an image of the object to be tested by calculation of the NMR signal. An image with a high SN can be obtained by using a high magnetic field generator as a static magnetic field in which the object to be tested is placed.

In recent years, a high magnetic field MRI apparatus capable of realizing a high magnetic field of 3 T or more has become widespread with the development of superconducting magnets. In the high magnetic field MRI, a high SN is obtained, but there is a problem in that brightness unevenness occurs in an image in abdominal imaging or the like. As one of the causes of this brightness unevenness, there is spatial non-uniformity of the magnetic field distribution (irradiation magnetic field distribution, B1 distribution) of high-frequency magnetic field pulses (hereinafter, referred to as RF pulses) to excite the nuclear spins in the tissue of the object. Generally, the resonance frequency of the high-frequency magnetic field for excitation is proportional to the static magnetic field strength. Accordingly, in the high magnetic field MRI, it is necessary to radiate a magnetic field of a frequency higher than that in the high-frequency magnetic field in the related art. In this case, the wavelength of the high-frequency magnetic field in the body becomes the same scale as the size of the body (particularly, abdomen). For this reason, the phase of the high-frequency magnetic field changes depending on the position in the body, and this change appears as image unevenness.

There is an RF shimming as a technique for solving the spatial non-uniformity of the irradiation magnetic field distribution (B1 distribution). In the RF shimming, the non-uniformity of the B1 distribution is reduced by controlling independently the intensity and phase of the RF pulse given to each channel using an RF coil for transmission with a plurality of channels. In order to determine the intensity and phase of the RF pulse given to each channel, the B1 distribution of each channel is required for each object and each imaging part, and various methods for measuring the B1 distribution have been proposed.

A typical method for measuring (B1 measurement) the B1 distribution is a method called a Double Angle Method (DAM), and the B1 distribution is measured by calculation of an image captured using an RF pulse with an arbitrary flip angle and an image captured using an RF pulse with a flip angle which is twice the arbitrary flip angle. In addition, a method for calculating the B1 distribution by acquiring a plurality of images using a plurality of RF pulses with different flip angles and performing the fitting of the signal intensities (pixel values) of the plurality of images according to the signal intensity expression determined by the pulse sequence has also been proposed (NPL 1). In addition, for a plurality of images acquired similarly, a method for calculating the B1 distribution from the period of signal intensity change has also been proposed (PTL 1).

In addition, a method for repeating the pulse sequence, which is for acquiring an image by applying a high-frequency magnetic field pre-pulse (hereinafter, simply referred to as a pre-pulse), while changing the intensity of the pre-pulse and calculating the B1 distribution from the acquired image (NPL 2) or a method for calculating the B1 distribution by taking the ratio between an image acquired immediately after pre-pulse application and an image acquired without applying the pre-pulse has also been proposed (NPL 3).

CITATION LIST

Patent Literature

[PTL 1] JP-A-2008-68830

Non Patent Literature

[NPL 1] Hai-King Margaret Cheng, Graham A Wright, "Rapid High-resolution T1 Mapping by Variable Flip Angles: Accurate and Precise Measurements in the Presence of Radiofrequency Field Inhomogeneity", Magnetic Resonance in Medicine 55: 566-574

[NPL 2] J. T. Vaughan, M. Garwood, C. M. Collins, W. Liu, L DelaBarre, G. Adriany, P. Andersen, H. Merkle, R. Goebel, M. B. Smith, K. Ugurbil, "7 T vs 4 T: RF Power, Homogeneity, and Signal-to-Noise Comparison in Head Images" Magnetic Resonance in Medicine 46: 24-30 (2001)

[NPL 3] H-P. Fautz, M. Vogel, P. Gross, A. Kerr, and Y. Zur, "B1 mapping of coil arrays for parallel transmission", Proc. Intl. Soc. Mag. Reson. Med. 16 (2008) 1247

[NPL 4] R. Lattanzi, C. Glaser, A. V. Mikheev, C. Petchprapa, D. J. Mossa, S. Gyftopoulos, H. Rusinek, M. Recht, and D. Kim, "A B1-insensitive High resolution, 2D T1 Mapping Pulse Sequence for Radial dGEMRIC of the Hip at 3 T", Prc. Intl. Soc. Mag. Reson. Med. 19 (2011) 504

[NPL 5] John G. Sled, G. Bruce Pike: Magnetic Resonance in Medicine 43: 589-593 (2000)

SUMMARY OF INVENTION

Technical Problem

However, there are following problems in the methods described above. In the Double Angle Method, in order to eliminate the influence of T1 relaxation, repetition time TR (RF pulse application interval) is generally set to a time of about 5 seconds. In this case, the B1 distribution can be calculated using a simple computation expression. However, a long imaging time is required, and the imaging time may be about 10 minutes or more. In the techniques disclosed in PTL 1 and NPL 1, since the T1 value is included in the function used for fitting, it is not necessary to eliminate the influence, and imaging can be performed in a relatively short TR. Accordingly, the imaging time can be shorter than that in the Double Angle Method. However, in order to find the period of fitting or signal intensity change, it is necessary to acquire images at about 20 different flip angles. Accordingly, there is a problem in that the imaging time is still long.

In addition, since the calculation accuracy depends on the number of imaging or the accuracy of fitting, a longer imaging time is required in order to calculate the B1 distribution with high accuracy.

In the technique disclosed in NPL 2, since the period of intensity change in the image signal, which is a basis for B1 distribution calculation, depends only on the flip angle of the pre-pulse, there is no influence according to the pulse sequence for acquiring image signals. Therefore, it is possible to set the TR in this pulse sequence to be short, and it is possible to reduce the imaging time compared with that in the Double Angle Method. However, since the period of the image signal intensity change according to the pre-pulse intensity change is calculated using the fitting, it is necessary to change the flip angle of the pre-pulse 20 times or more in order to calculate the B1 distribution with high accuracy. Accordingly, there is a problem in that the imaging time is still long. In addition, complicated computation is required to calculate the B1 distribution.

In the technique disclosed in NPL 3, the B1 distribution can be calculated at high speed by setting the time (TI) from the application of the pre-pulse to the acquisition of an echo signal (NMR signal) as short as possible. However, since the computation expression uses the approximation that can only be used with TI=0, there is a problem in that error is increased when the TI is long.

Therefore, it is an object of the present invention to provide an MRI apparatus capable of measuring the B1 distribution in a short time with high accuracy.

Solution to Problem

The present invention is intended to propose a new method in which, for B1 distribution measurement, the application of a pre-pulse and a signal acquisition pulse sequence are combined and a plurality of signal acquisition pulse sequences with different elapsed time (TI) from the pre-pulse application are executed, and the B1 is calculated by calculation of several images (data for images) with different TI.

That is, an MRI apparatus of the present invention includes: an RF radiation unit that radiates a high-frequency magnetic field (B1) to cause nuclear magnetic resonance in an object; an imaging unit that images the object using a B1 distribution measurement sequence that includes a signal acquisition sequence to acquire an echo signal by setting elapsed time (TI) from application of a pre-pulse; and a calculation unit that reconstructs an image of the object using the echo signal and is characterized in that the calculation unit calculates an irradiation magnetic field distribution of the RF radiation unit using the image and the calculation unit calculates the irradiation magnetic field distribution using a plurality of images with the different elapsed time.

An irradiation magnetic field measuring method of the present invention includes: a measurement step of executing a signal acquisition sequence to acquire an echo signal by setting elapsed time (TI) from application of a pre-pulse by an RF radiation unit; an image reconstruction step of reconstructing an image of the object using an echo signal; and an irradiation magnetic field distribution calculation step of calculating the irradiation magnetic field distribution of the RF radiation unit using the image and is characterized in that, in the irradiation magnetic field distribution calculation step, the irradiation magnetic field distribution is calculated using a plurality of images with the different elapsed time.

Advantageous Effects of Invention

According to the present invention, by the combination of the pre-pulse and the plurality of signal acquisition sequences with different elapsed time from the pre-pulse application, it is possible to measure (B1 measurement) the magnetic field distribution of the RF pulse in a very short time with high accuracy. High-accuracy RF shimming can be realized by controlling the RF radiation means using the measured magnetic field distribution.

In addition, since the calculation means solves the determinant using the ratio between the signal intensity of the image with no pre-pulse and the signal intensity of the image with a pre-pulse, it is possible to calculate not only the B1 distribution but also the T1 distribution when calculating the irradiation magnetic field distribution.

DESCRIPTION OF EMBODIMENTS

Hereinafter, embodiments of the present invention will be described. First, the overall configuration of an MRI apparatus to which the present invention is applied will be described with reference to the drawings.

Figure 1:
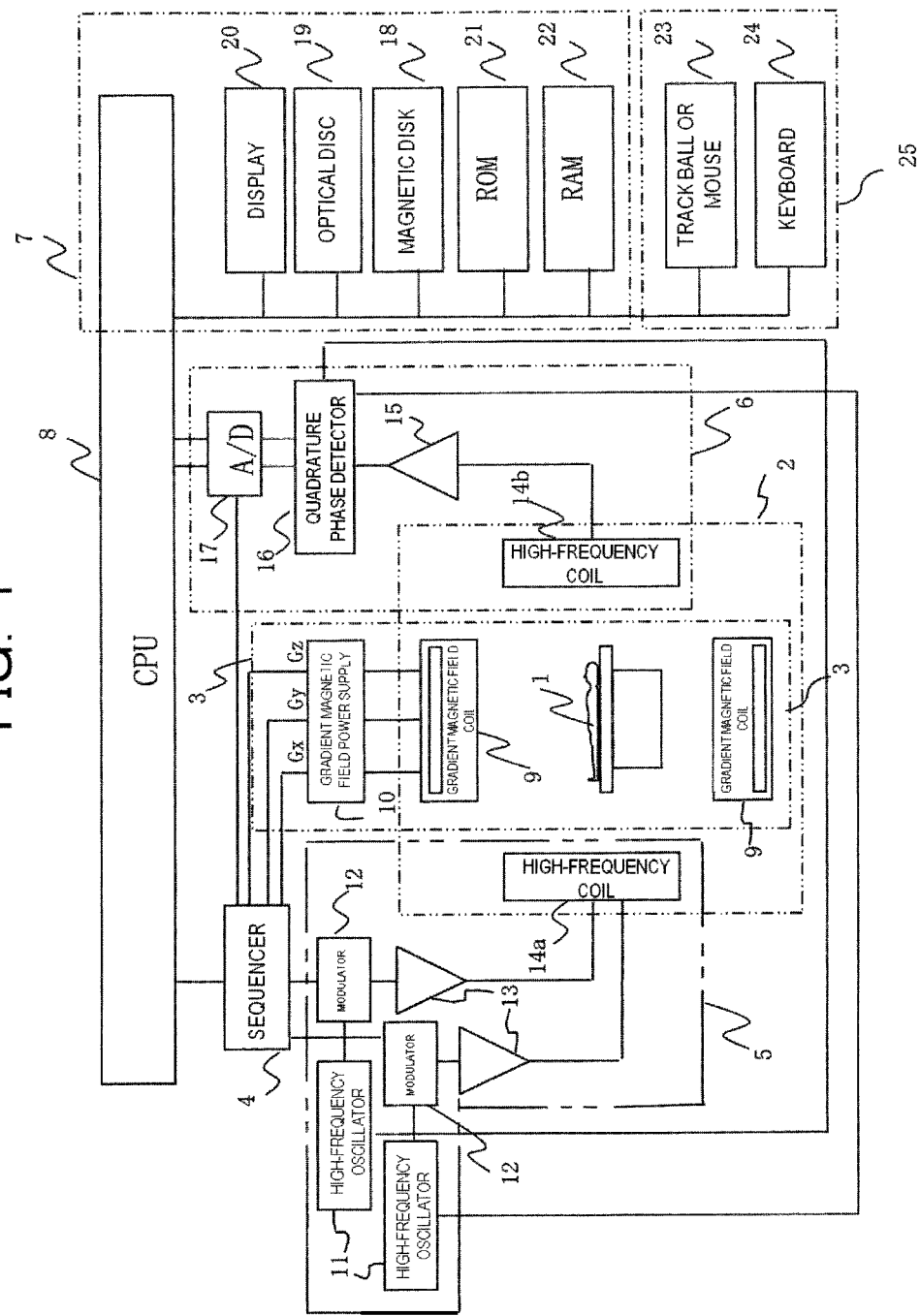
FIG. 1 is a block diagram showing an embodiment of an MRI apparatus to which the present invention is applied.

FIG. 1 is a block diagram showing an embodiment of the MRI apparatus to which the present invention is applied. This MRI apparatus is configured to include a static magnetic field generation system 2, a gradient magnetic field generation system 3, a signal transmission system 5, a signal receiving system 6, a signal processing system 7, a sequencer 4, and a central processing unit (CPU) 8.

The static magnetic field generation system 2 generates a uniform static magnetic field in space where an object 1 is placed, and is configured to include a permanent magnet type, a normal conducting type, or a superconducting type static magnetic field generator (not shown). The static magnetic field generator is disposed so as to generate a uniform static magnetic field in a direction perpendicular to the body axis of the object 1 in the case of a vertical magnetic field method and in the body axis direction in the case of a horizontal magnetic field method.

The gradient magnetic field generation system 3 is configured to include a gradient magnetic field coil 9 that applies a gradient magnetic field in three orthogonal axial directions of X, Y, and Z, which are the coordinate system (stationary coordinate system) of the MRI apparatus, and a gradient magnetic field power supply 10 to drive each gradient magnetic field coil. Desired gradient magnetic fields Gx, Gy, and Gz can be applied in the three axial directions of X, Y, and Z by driving the gradient magnetic field power supply 10 of each coil according to the command from the sequencer 4 to be described later. According to the method for applying the gradient magnetic field, an imaging slice of the object can be selectively excited, and positional information can be added to the echo signal (NMR signal) generated from the excitation region.

The sequencer 4 is control means for repeatedly applying RF pulses and gradient magnetic field pulses according to the predetermined pulse sequence, and operates under the control of the CPU 8 and transmits various commands, which are required to collect the data of a tomographic image of the object 1, to the signal transmission system 5, the gradient magnetic field generation system 3, and the signal receiving system 6.

The signal transmission system 5 emits RF pulses to the object 1 in order to cause nuclear magnetic resonance in the nuclear spins of atoms which form the body tissue of the object 1, and is configured to include a high-frequency oscillator 11, a modulator 12, a high-frequency amplifier 13, and a transmission-side high-frequency coil (transmission coil) 14a. In the present embodiment, the transmission coil is configured to have a plurality of feeding points and to be able to adjust the intensity and the phase of the supplied high-frequency wave. A plurality of high-frequency oscillators 11, a plurality of modulators 12, and a plurality of high-frequency amplifiers 13 are provided corresponding to respective channels. Although the case where there are two feeding points is shown in the drawing, the number of feeding points is not limited to 2.

RF pulses output from the high-frequency oscillator 11 are amplitude-modulated by the modulator 12 at the timing according to the command from the sequencer 4, and the amplitude-modulated RF pulses are amplified by the high-frequency amplifier 13 and are then supplied to the high-frequency coil 14a disposed adjacent to the object 1. As a result, RF pulses are emitted to the object 1. The timing from the sequencer 4 and the modulation of the modulator 12 are controlled reflecting the measurement result of the B1 distribution to be described later.

The signal receiving system 6 detects an echo signal emitted by nuclear magnetic resonance of the nuclear spins, which form the body tissue of the object 1, and is configured to include a receiving-side high-frequency coil (receiving coil) 14b, a signal amplifier 15, a quadrature phase detector 16, and an A/D converter 17. The NMR signal of the response of the object 1 induced by the electromagnetic waves emitted from the transmission coil 14a is detected by the signal receiving coil 14b disposed adjacent to the object 1 and is amplified by the signal amplifier 15. Then, at the timing according to the command from the sequencer 4, the amplified signals are divided into signals of two systems perpendicular to each other by the quadrature phase detector 16, and each signal is converted into a digital amount by the A/D converter 17 and is transmitted to the signal processing system 7.

In addition, although the configuration where the high-frequency coil for transmission and the high-frequency coil for reception are separately provided is shown in FIG. 1, it is also possible to adopt a configuration where one high-frequency coil (including multiple coils) is used as a high-frequency coil for transmission and a high-frequency coil for reception.

The signal processing system 7 performs display, storage, and the like of various kinds of data processing and processing results, and includes an external storage device, such as an optical disc 19 or a magnetic disk 18, and a display 20, such as a CRT. When data from the signal receiving system 6 is input to the CPU 8, the CPU 8 executes processing, such as signal processing and image reconstruction, and displays a tomographic image of the object 1, which is the result, on the display 20 and also records the tomographic image on the magnetic disk 18 or the like of the external storage device.

The CPU 8 has not only a function as a calculation unit of the signal processing system 7 but also a function as a control unit that controls each component of the apparatus, and allows various pulse sequences to be executed through the sequencer 4. The pulse sequence is included as a program in advance. In the present embodiment, a B1 distribution measurement sequence for measuring the irradiation magnetic field distribution (B1 distribution) by the transmission coil is included. In addition, the signal processing system 7 calculates the B1 distribution or calculates the phase or amplitude of the high-frequency pulse applied to the transmission coil using the measurement result of the B1 distribution measurement sequence, and controls the phase or amplitude of the high-frequency pulse applied to the transmission coil on the basis of this calculation result.

An operating unit 25 inputs various kinds of control information regarding the MRI apparatus or control information regarding the processing performed in the signal processing system 7, and is configured to include a track ball or mouse 23 and a keyboard 24. This operating unit 25 is disposed adjacent to the display 20, so that the operator controls various kinds of processing of the MRI apparatus interactively through the operating unit 25 while observing the display 20.

In addition, in FIG. 1, the transmission-side high-frequency coil 14a and the gradient magnetic field coil 9 are provided in the static magnetic field space of the static magnetic field generation system 2, into which the object 1 is inserted, such that they face the object 1 in the case of a vertical magnetic field method and they surround the object 1 in the case of a horizontal magnetic field method. In addition, the receiving-side high-frequency coil 14b is provided so as to face or surround the object 1.

Figure 2:
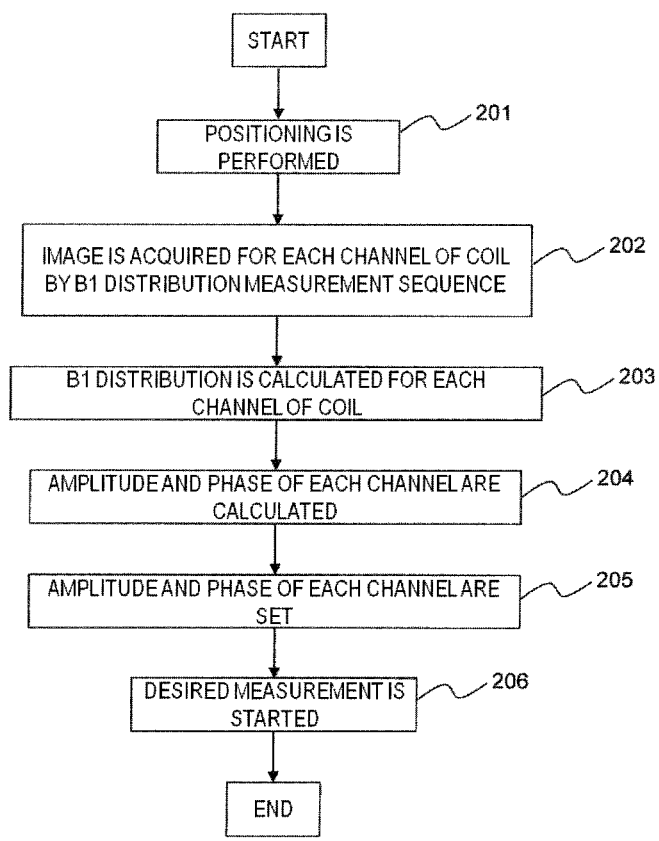
FIG. 2 is a flow chart showing an embodiment of the B1 distribution measurement procedure according to the present invention.

Next, the procedure of measuring the B1 distribution in the above MRI apparatus will be described. FIG. 2 shows the procedure.

First, an object is placed in static magnetic field space, and is positioned such that a target imaging part is positioned approximately in the center of the static magnetic field space (step 201). Then, for each channel of the transmission coil, the B1 distribution measurement sequence is executed to acquire an image (step 202). The B1 distribution measurement sequence will be described later. The B1 distribution for each channel is calculated using the image acquired in step 202 (step 203). The amplitude and phase of a high-frequency pulse applied to the channel are set using the calculated B1 distribution (steps 204 and 205). Then, desired measurement (imaging) is performed in the conditions set in step 204 (step 206). Hereinafter, a typical embodiment of B1 distribution measurement will be described in detail. Since step 201 and steps from step 204 are common in embodiments described below, steps 202 and 203 will be described for each embodiment.

First Embodiment

B1 Distribution Measurement (Step 202)

The B1 distribution measurement sequence is a combination of a pre-pulse, which is an RF pulse having a relatively large flip angle, and a signal acquisition sequence using an RF pulse having a small flip angle. In the signal acquisition sequence, a plurality of images with different elapsed time (TI) after pre-pulse application are obtained. Depending on the combination method of the pre-pulse and the signal acquisition sequence, different embodiments are possible. According to the embodiments, the calculation of the B1 distribution changes (step 203).

The present embodiment is characterized in that at least three signal acquisition sequences are executed subsequent to the application of the pre-pulse and the B1 distribution is calculated from the image acquired in each signal acquisition sequence.

Figure 3:
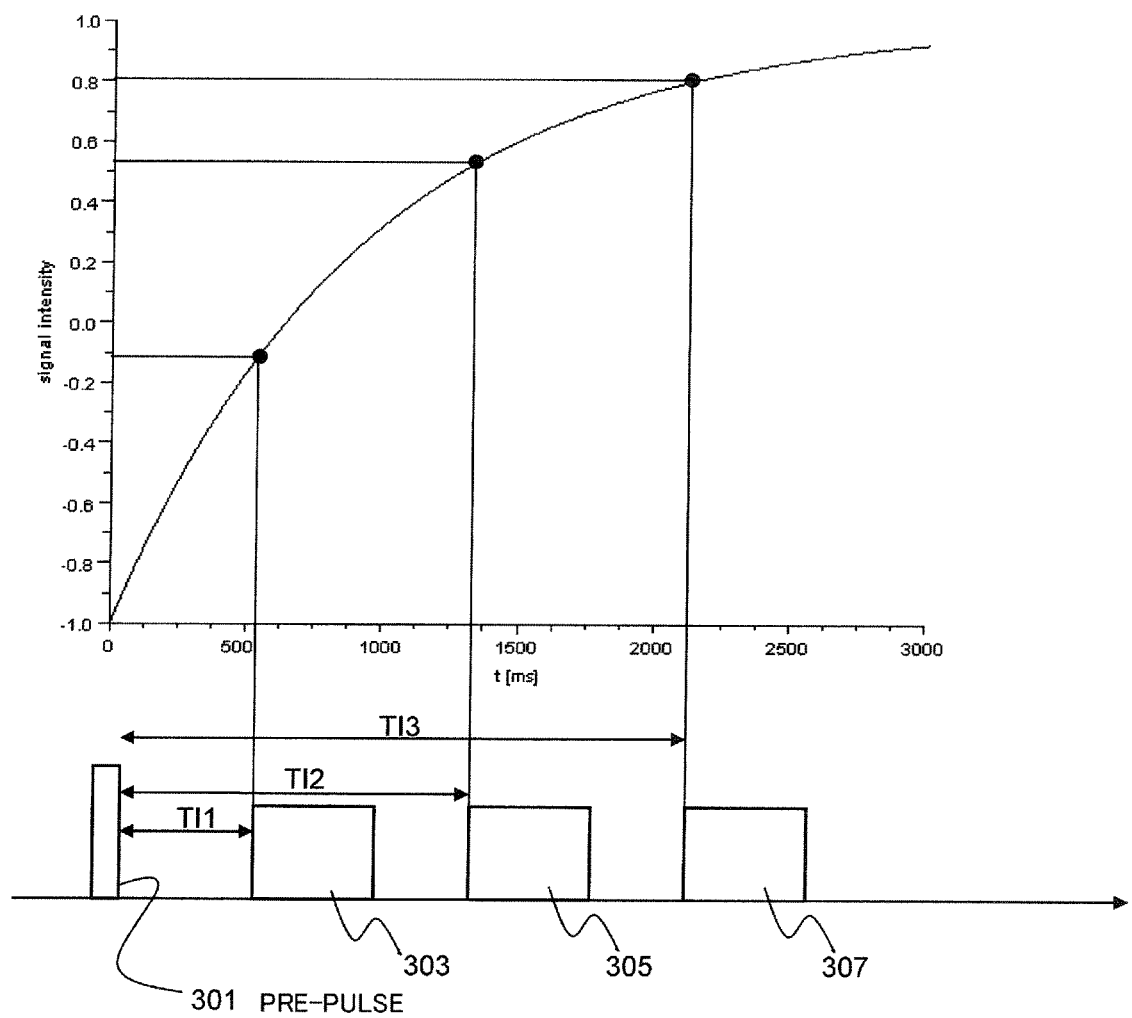
FIG. 3 is a diagram showing a first embodiment of the B1 distribution measurement sequence.

FIG. 3 is a diagram showing the relationship between a pre-pulse 301 and signal acquisition sequences 303, 305, and 307. On the upper side in FIG. 3, a change in the signal intensity depending on the elapsed time (TI) from the application of the pre-pulse 301 is shown as a graph. In the graph shown in FIG. 3, the horizontal axis indicates elapsed time after the application of pre-pulse, and the vertical axis indicates signal intensity. For example, the pre-pulse 301 is a non-selective RF pulse. For example, the pre-pulse 301 is a 90° pulse having a large flip angle. At least three signal acquisition sequences 303, 305, and 307 are executed while the nuclear spins excited by the pre-pulse 301 relax longitudinally, thereby obtaining three pieces of k-space data (or image data) of different TI. In addition, in the present invention, it is important to obtain data having different longitudinal relaxation from the pre-pulse, and the TI is set such that all signal acquisition sequences are completed while the influence of the pre-pulse remains sufficiently. In this manner, it is possible to calculate the B1 distribution with high accuracy.

Each signal acquisition sequence is not particularly limited as long as it is a pulse sequence capable of collecting k-space data in a short time. For example, a gradient echo (GrE) based pulse sequence shown in FIG. 4 can be adopted. In this GrE-based sequence, an RF pulse 401 having a small flip angle is applied together with a slice gradient magnetic field pulse 402, and then a phase encoding gradient magnetic field 403 is applied. At the same time, a readout gradient magnetic field 404 is applied, and an echo signal 405 is measured during the application of the readout gradient magnetic field with reversed polarity. Finally, a gradient magnetic field 406 for rephase is applied in a phase encoding direction. In order to reduce the influence on the longitudinal magnetization, a small flip angle pulse of preferably 10° or less, and more preferably 5° or less is used as the RF pulse 401.

In this pulse sequence, a small flip angle pulse is used as the RF pulse 401, and a rephase pulse 406 in the phase encoding direction is used. Accordingly, repetition time TR can be set to about several milliseconds. The RF pulse 401 to the rephase gradient magnetic field 406 are repeated while changing the intensity of the phase encoding gradient magnetic field pulse 403, thereby obtaining the data (k-space data) of the slice selected by the slice gradient magnetic field 402.

The k-space data is used for the calculation of the B1 distribution, which will be described later, and the matrix size is preferably about 64×64. Then, it is possible to acquire all pieces of k-space data in a very short time, specifically, in the measurement time of about 200 ms.

Since the contrast of the image data formed from the k-space data is mainly dominated by the data in the center of k-space data, the timing to measure the echo of the center of k-space data in each signal acquisition sequence is set as the elapsed time (TI) from the pre-pulse application. In the embodiment shown in FIG. 3, each signal acquisition sequence is a so-called centric-order pulse sequence in which the measurement starts from the echo in the center of k-space, and start points of the signal acquisition sequence are TI1, TI2, and TI3. In addition, in the present embodiment, the relationship of the elapsed time is set as the relationship of TI2=2×TI1 and TI3=3×TI1.

B1 Distribution Calculation (Step 203)

Next, a method for calculating the B1 distribution from the k-space data obtained by the B1 distribution measurement sequence shown in FIG. 3 will be described.

The signal intensity S(B1, TI) of a certain observed pixel of image data, which is obtained by performing an inverse Fourier transform of the k-space data obtained by the first signal acquisition sequence, is given by Expression (1).

$$S(B1,TI)=S_{seq}(1-(1-\cos(B1\cdot\alpha))\exp(-TI/T1)) \quad (1)$$

In Expression (1), Sseq indicates the signal intensity determined by the signal acquisition sequence after pre-pulse, $\alpha$ indicates the flip angle of the set pre-pulse, TI indicates time until signals in the center of k-space are collected from the pre-pulse application, and T1 indicates longitudinal relaxation time depending on the tissue.

Similarly, the signal intensity of the observed pixel of the image data obtained from the second and third signal acquisition sequences can be expressed as in Expressions (2) and (3).

$$S(B1,2TI)=S_{seq}(1-(1-\cos(B1\cdot\alpha))\exp(-2TI/T1)) \quad (2)$$

$$S(B1,3TI)=S_{seq}(1-(1-\cos(B1\cdot\alpha))\exp(-3TI/T1)) \quad (3)$$

Here, if $1-\cos(B1\cdot\alpha)\equiv X$ and $\exp(-TI/T1)\equiv Y$ are defined, Expressions (1) to (3) can be written as Expressions (4) to (6).

$$S(B1,TI)=S_{seq}(1-XY) \quad (4)$$

$$S(B1,2TI)=S_{seq}(1-XY^2) \quad (5)$$

$$S(B1,3TI)=S_{seq}(1-XY^3) \quad (6)$$

By solving the simultaneous equations of Expressions (4) to (6), X and Y are calculated from Expressions (7) and (8).

$$X = \frac{[S(B1, TI) - S(B1, 2TI)]^3}{[S(B1, 2TI) - S(B1, 3TI)][\{S(B1, 2TI)\}^2 - S(B1, TI)S(B1, 3TI)]} \quad (7)$$

-continued $$Y = \frac{S(B1, 2TI) - S(B1, 3TI)}{S(B1, TI) - S(B1, 2TI)} \quad (8)$$

Here, since $X=1-\cos(B1 \cdot \alpha)$ from the definition, B1 can be calculated as in Expression (9).

$$B1 = \frac{\arccos(1 - X)}{\alpha} \quad (9)$$

In the present embodiment, since the B1 distribution can be calculated by solving the simultaneous equations from the images, which are obtained by performing at least three signal acquisition sequences with different TI, the B1 distribution can be measured in a very short time, such as several seconds.

As described above, since the B1 distribution can be accurately calculated by solving the simultaneous equations from multiple measurement results (signal intensities) of different TI, it is also preferable in terms of the ease of operation. However, the B1 distribution may also be calculated by fitting the multiple measurement results.

In addition, in order to solve the simultaneous equations described above, at least three images (three executions of the signal acquisition sequence) are required. However, three or more times are also possible in the range of longitudinal spin relaxation time after the pre-pulse application. In addition, although the TI ratio of the plurality of signal acquisition sequences is set as the integer ratio in the example described above, the TI ratio of the plurality of signal acquisition sequences may be a non-integer ratio as long as the plurality of signal acquisition sequences has different TI.

Figure 4:
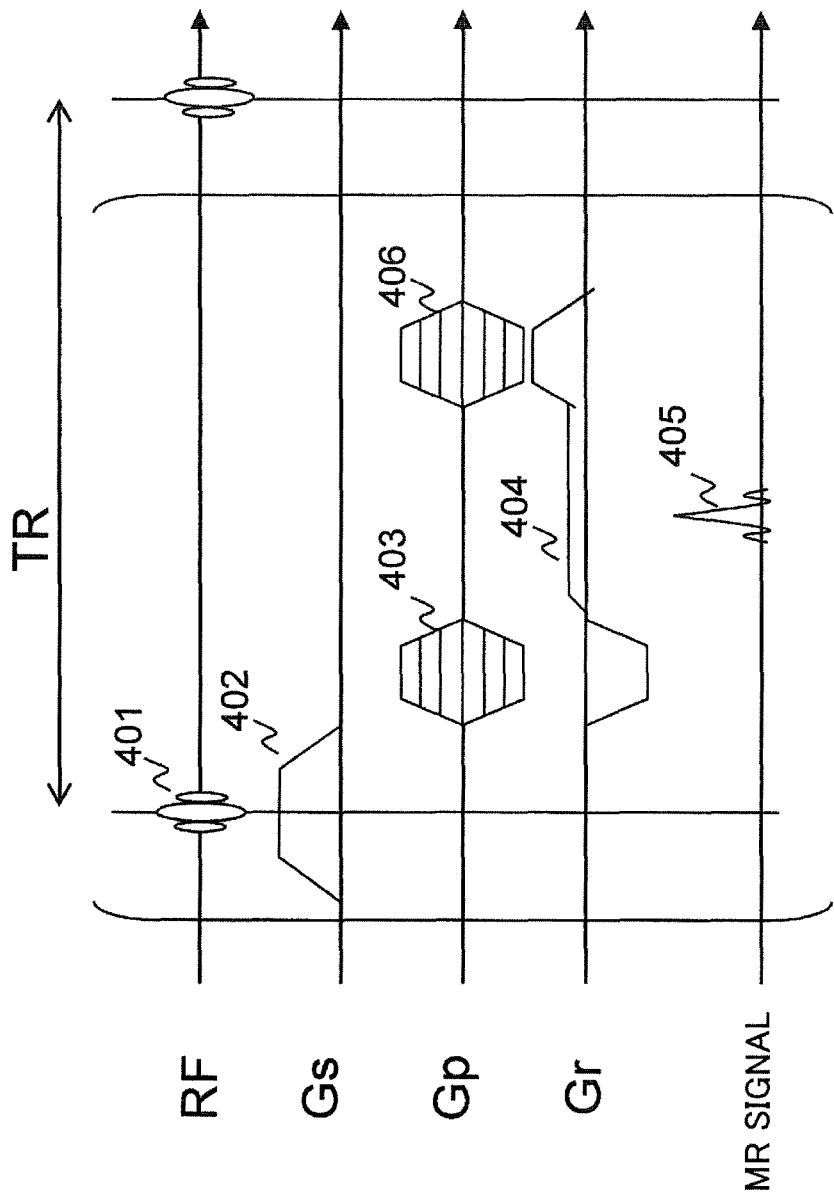
FIG. 4 is a timing chart showing an example of the signal acquisition sequence.

The signal acquisition sequence is not limited to the sequence shown in FIG. 4 as long as the image data is acquired in a short time, and various changes may be made.

For example, a plurality of signal acquisition sequences may be continuously executed without setting the interval, instead of executing the three signal acquisition sequences with different TI shown in FIG. 3 at fixed intervals. Alternatively, before and after the signal acquisition sequence, an RF pulse (301 in FIG. 3) may be continuously applied during the same TR as the signal acquisition sequence without measuring the echo. In these modifications, the occurrence of the contrast difference within the signal acquisition sequence can be suppressed by applying RF pulses continuously to maintain the spin in a steady state.

In addition, although the GrE based pulse sequence using a phase encoding pulse in one direction is shown in FIG. 4, it is also possible to adopt a pulse sequence of a so-called radial method to scan k-space radially by combining the encoding pulses in two axial directions.

Figure 5:
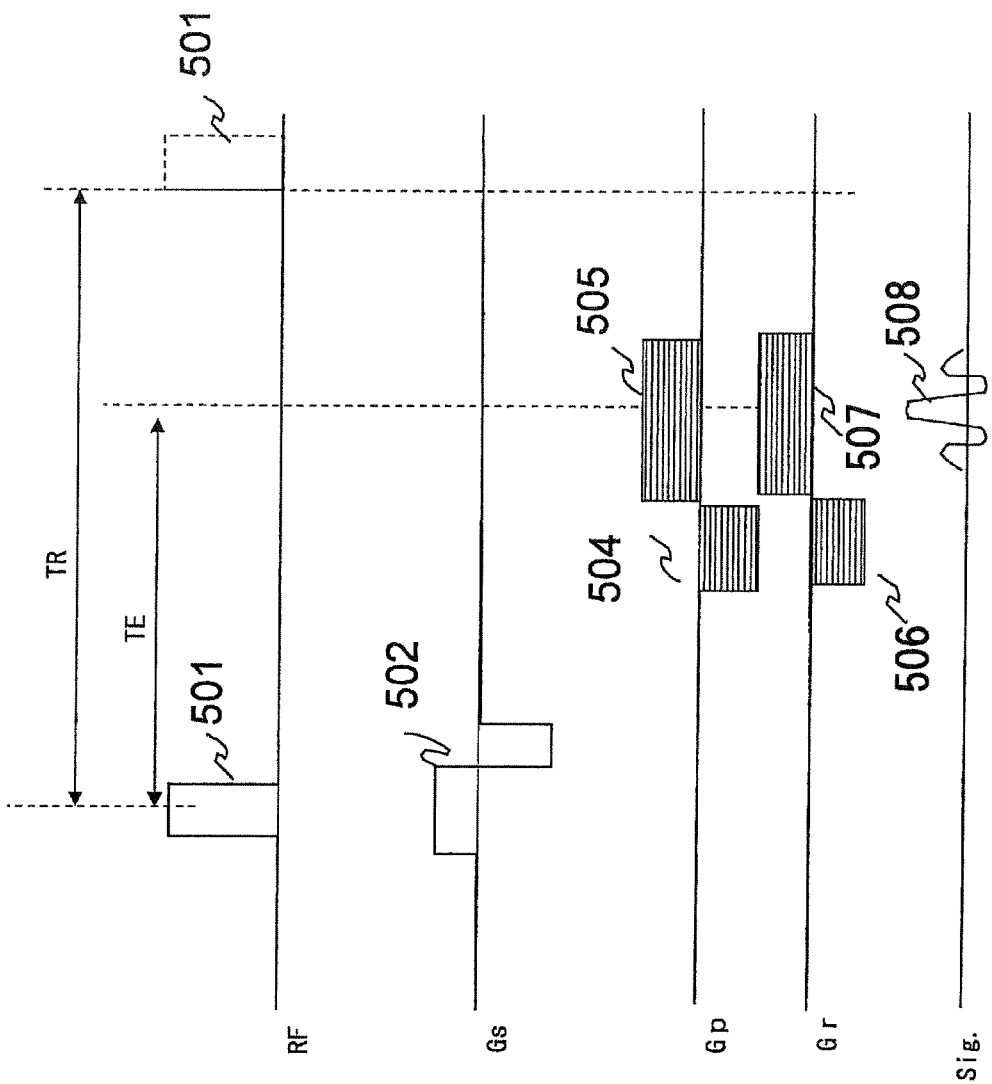
FIG. 5 is a timing chart showing another example of the signal acquisition sequence.

FIG. 5 shows an example of the pulse sequence of the radial method. In this signal acquisition sequence, an RF pulse 501 is applied together with a slice gradient magnetic field pulse 502. Then, gradient magnetic field pulses 504 and 506 and gradient magnetic field pulses 505 and 507 having reversed polarity are applied in two axial directions (Gp and Gr directions), and a gradient echo signal 508 that reaches its peak when the absolute value of the amount of application of each of the gradient magnetic field pulses 504 and 506 becomes equal to the absolute value of the amount of application of each of the gradient magnetic field pulses 505 and 507 is measured. Time until the echo signal is generated from excitation, that is, the echo time TE is a parameter to determine the image contrast, and may be arbitrarily set according to the purpose of imaging.

Data obtained by arranging one measured echo signal 508 in k-space becomes a column of data (spoke) which passes through the origin of k-space and in which the angle of k-space with respect to the coordinate axes is determined by the amount of application of the gradient magnetic field pulses in the two axial directions. By repeating the above step every repetition time TR while changing the amount of application and the ratio of the gradient magnetic field pulses in the two axial directions, it is possible to acquire the data while rotating the k-space. Also when this pulse sequence is adopted, it is possible to obtain a piece of k-space data in the order of 0.1 seconds even if the number of repetitions is set to 200 (the number of spokes is set to 200) by setting the flip angle of the RF pulse 501 to be equal to or less than 10° and setting TR to about several milliseconds.

In the pulse sequence of the radial method, data of each spoke passes through the center of k-space. Accordingly, the signal intensity expressed as in Expression (1) is an average value of the influence of the longitudinal relaxation until the acquisition of the last spoke from the acquisition of the first spoke of all pieces of data. However, since the acquisition time of all pieces of data is short as described above, the B1 distribution can be calculated by the calculation of (1) to (9) in the same manner as when the signal acquisition sequence shown in FIG. 4 is used.

As another modification, it is also possible to adopt a 3D pulse sequence (FIG. 6) obtained by adding the slice encoding gradient magnetic field added to the slice axis (Gs) of the signal acquisition sequence shown in FIG. 4. By using the 3D pulse sequence, it becomes possible to measure the three-dimensional B1 distribution.

Second Embodiment

B1 Distribution Measurement (Step 202)

The present embodiment is characterized in that the B1 distribution is calculated from at least three images acquired by executing the signal acquisition sequence for images (first B1 distribution measurement sequence) at least twice with different elapsed time from the pre-pulse application and also executing the signal acquisition sequence (second B1 distribution measurement sequence) of different pre-pulse application conditions from the first B1 distribution measurement sequence.

FIG. 7(a) is a diagram showing the relationship between a first B1 distribution measurement sequence 710 and a second B1 distribution measurement sequence 720. The first B1 distribution measurement sequence 710 is configured to include a pre-pulse 711, which is an RF pulse having a flip angle of 90° or more, and at least two signal acquisition sequences 713 and 715 subsequent to the pre-pulse 711, as in the first embodiment shown in FIG. 3. However, two or more signal acquisition sequences 713 and 715 are sufficient in the present embodiment while at least three signal acquisition sequences have been executed within the longitudinal relaxation time of the spin after the application of the pre-pulse 711 in the first embodiment.

The second B1 distribution measurement sequence 720 is configured to include a single signal acquisition sequence 721 that does not use a pre-pulse. In FIG. 7(a), the second B1 distribution measurement sequence 720 is arranged before the first B1 distribution measurement sequence 710. However, as shown in FIG. 7(b), the second B1 distribution measurement sequence 720 may be arranged after the passage of longitudinal relaxation time TD after the first B1 distribution measurement sequence 710.

Similar to the first embodiment, any kind of signal acquisition sequences 713, 715, and 721 can be used if they are pulse sequences capable of collecting k-space data in a short time. For example, the GrE based pulse sequence shown in FIG. 4 or 5 may be adopted.

B1 Distribution Calculation (Step 203)

Next, a method for calculating the B1 distribution from the k-space data obtained by the B1 measurement pulse sequence shown in FIG. 7 will be described.

The second B1 distribution measurement sequence 720 (signal acquisition sequence 721) can be regarded as a signal acquisition sequence using a pre-pulse having a flip angle of 0°. Accordingly, the signal intensity of a certain observed pixel of the acquired image is given by Expression (10) assuming that α=0° in Expression (1).

$$S_0 = Sseq \qquad (10)$$

On the other hand, in the first signal acquisition sequences 713 and 715 to acquire the central data of k-space assuming that the flip angle of the pre-pulse 711 is α and the elapsed time from the application of the pre-pulse 711 is TI and TI×2, the signal intensity of an observed pixel is given by Expressions (11) and (12).

$$\frac{S(B1, TI)}{S_0} = 1 - (1 - \cos(B1 \cdot \alpha))\exp(-TI/T1)) \qquad (11)$$

$$\frac{S(B1, 2TI)}{S_0} = 1 - (1 - \cos(B1 \cdot \alpha))\exp(-2TI/T1)) \qquad (12)$$

Expressions (11) and (12) are transformed into Expressions (13) and (14), respectively.

$$(1 - \cos(B1 \cdot \alpha))\exp(-TI/T1)) = 1 - \frac{S(B1, TI)}{S_0} = \qquad (13)$$

$$(1 - \cos(B1 \cdot \alpha))\exp(-2TI/T1)) = 1 - \frac{S(B1, 2TI)}{S_0} = \qquad (14)$$

By squaring Expression (13) and dividing it by Expression (14), the B1 distribution is calculated from Expression (15).

$$B1 = \frac{\arccos\left(1 - \frac{(S_0 - S(B1, TI))^2}{S_0(S_0 - S(B1, 2TI))}\right)}{\alpha} \qquad (15)$$

Figure 7:
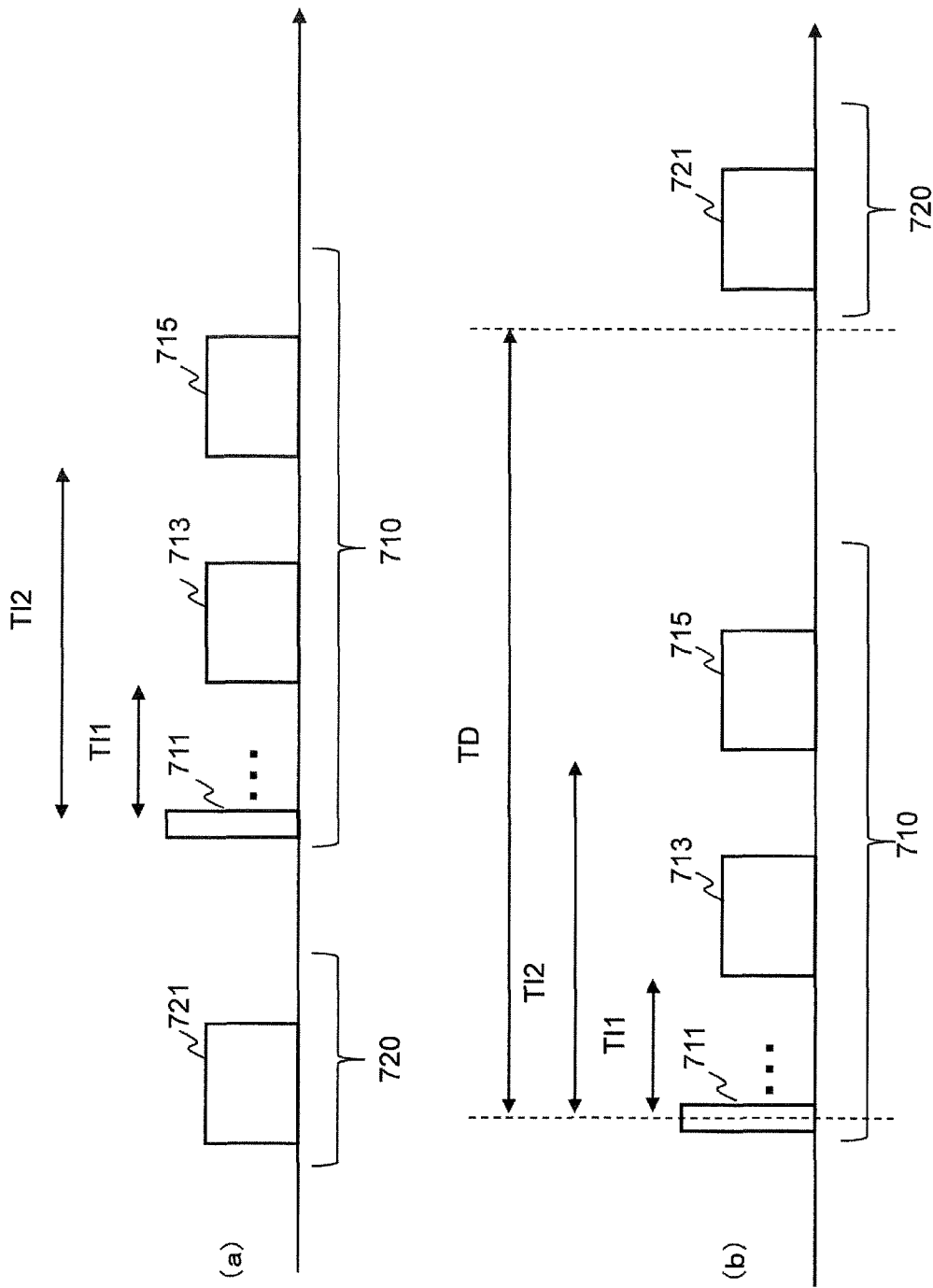
FIG. 7($a$) is a diagram showing a second embodiment of the B1 distribution measurement sequence, and FIG. 7($b$) is a diagram showing a modification of FIG. 7($a$).
Figure 8:
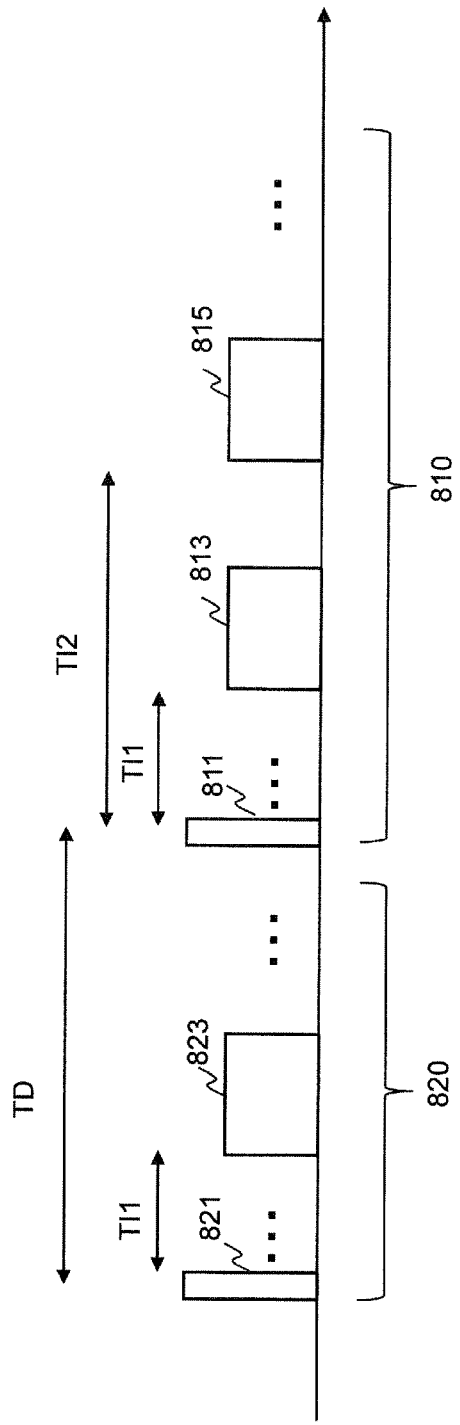
FIG. 8 is a diagram showing a second embodiment of the B1 distribution measurement sequence that is generalized.

In addition, in the example shown in FIG. 7, the second B1 distribution measurement sequence is configured to include a signal acquisition sequence that does not use a pre-pulse. In the present embodiment, however, the pre-pulse application conditions (flip angles) in the first and second B1 distribution measurement sequences are different, and at least three signal acquisition sequences may be executed. For example, as shown in FIG. 8, a first B1 distribution measurement sequence 810 may be configured to include the application of a pre-pulse 811 of the first flip angle and two signal acquisition sequences 813 and 815, and a second B1 distribution measurement sequence 820 may be configured to include the application of a pre-pulse 821 of the second flip angle, which is different from the first flip angle, and one signal acquisition sequence 823. Although the relationship between the first and second flip angles is not particularly limited, for example, combinations of 90° and 0°, 90° and 180°, and the like may be adopted.

In addition, in the drawing, the order of the first B1 distribution measurement sequence 810 and the second B1 distribution measurement sequence 820 may be changed. In any case, it is desirable to set the interval between the first measurement and the second measurement (pre-pulse application interval TD) to be equal to or greater than the longitudinal relaxation time. In this manner, it is possible to improve the accuracy of B1 distribution measurement.

According to the present embodiment, compared with the technique disclosed in NPL 2, the imaging time can be reduced to [2÷(number of times of flip angle change in NPL 2)] since a flip angle changes once. In addition, compared with the first embodiment, the B1 distribution can be measured more accurately since the flip angle data is also used.

In addition, when repeating the B1 distribution measurement sequence, the next pre-pulse may be applied in an insufficiently relaxed state if the interval (pre-pulse application interval TD) is shortened. As a result, there is a possibility that the error of the calculation using Expressions (10) to (15) will be increased. This problem can be solved by setting TD to be equal to or greater than the longitudinal relaxation time as described above. However, it is also possible to add an RF pulse, which relaxes longitudinally, forcibly after the last signal acquisition sequence in the B1 distribution measurement sequence and to shorten the pre-pulse application interval. As the RF pulse that is forced to relax longitudinally, it is possible to use an RF pulse having the same intensity as a pre-pulse and a reverse phase of the phase of the pre-pulse. By using such a forcible longitudinal relaxation pulse, the B1 distribution can be calculated with high accuracy even if the imaging time is reduced.

Third Embodiment

B1 Distribution Measurement (Step 202)

The present embodiment is characterized in that a reference image acquisition sequence, in which a signal is acquired without applying a pre-pulse, is executed and a plurality of signal acquisition sequences having different time TI until the signal in the center of k-space is acquired from pre-pulse application are executed after the pre-pulse application and that the B1 distribution is calculated by the matrix operation using a reference image and a plurality of images of different TI.

Figure 9:
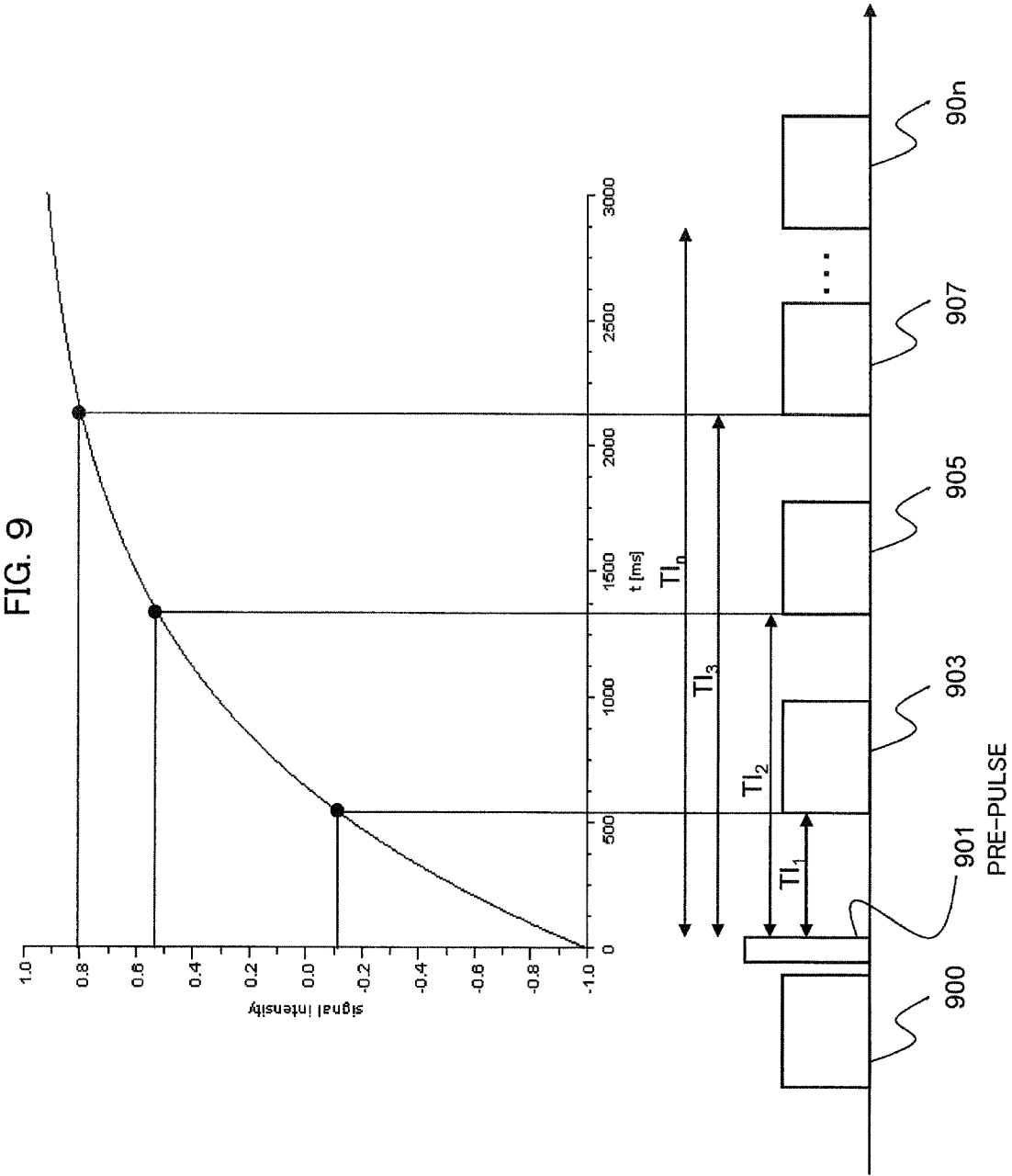
FIG. 9 is a diagram showing a third embodiment of the B1 distribution measurement sequence.

FIG. 9 shows the relationship between the pre-pulse and the signal acquisition sequence in the present embodiment. FIG. 9 is similar to FIG. 7 showing the relationship between the pre-pulse and the signal acquisition sequence. In the present embodiment, however, the signal acquisition sequence is a sequence of short TI to acquire a signal while the influence of a pre-pulse is large, and the ratio between TI of the first signal acquisition sequence and TI of the subsequent signal acquisition sequence is not limited to the integer ratio while the ratio between TI of the first signal acquisition sequence and TI of the subsequent signal acquisition sequence is the integer ratio.

Similar to the first embodiment, the signal acquisition sequences 903, 905, 907, . . . can be regarded as a gradient echo based pulse sequence of short TR as shown in FIG. 4. Accordingly, it is preferable that the signal acquisition sequences 903, 905, 907, . . . be centric-order sequences and the flip angle be set to be small. A pre-pulse 901 is a non-selective RF pulse having a large flip angle. A reference image acquisition sequence 900 is the same pulse sequence as the signal acquisition sequence 903 and the like, and it is preferable to execute the reference image acquisition sequence 900 immediately before the application of the pre-pulse 901 in order to reduce the imaging time.

B1 Distribution Calculation (Step 203)

Next, the calculation of the B1 distribution using images acquired by the reference image acquisition sequence 900 and the signal acquisition sequences will be described.

The signal intensity of an observed pixel of an image, which is reconstructed from a signal acquired in the k-th signal acquisition sequence (k=1, 2, 3, ..., n) after pre-pulse application, is given by the same Expression (16) as Expression (1) shown in the first embodiment assuming that the k-th TI is $TI_k$.

$$S(B1, TI_k) = S_{seq}(1 - (1 - \cos(B1 \cdot \alpha))\exp(-TI_k/T1)) \quad (16)$$

In Expression (16), the same reference numeral as in Expression (1) has the same meaning.

On the other hand, the signal intensity of the same observed pixel of the image obtained by the reference image acquisition sequence immediately before the pre-pulse is given by the same Expression (17) as Expression (10) since it is the same as when α=0 in Expression (16).

$$S_0 = S_{seq} \quad (17)$$

If Expression (16) is divided by Expression (17) and the natural logarithm is taken, it can be expressed as a linear combination of $\log(1-\cos(B1\cdot\alpha))$ and $(-TI_k/T1)$ as in Expression (18).

$$\log\left(1 - \frac{S(B1, 2TI_k)}{S_0}\right) = \log(1 - \cos(B_1 \cdot \alpha)) - \frac{TI_k}{T_1} \quad (18)$$

If the same calculation is performed for an image with different TI obtained from each signal acquisition sequence, the simultaneous equations of Expression (19) are obtained.

$$S = A \cdot X \quad (19)$$

$$S = \begin{pmatrix} W_1 \cdot \log\left(1 - \frac{S(B_1, TI_1)}{S_0}\right) \\ W_2 \cdot \log\left(1 - \frac{S(B_1, TI_2)}{S_0}\right) \\ W_3 \cdot \log\left(1 - \frac{S(B_1, TI_3)}{S_0}\right) \\ W_4 \cdot \log\left(1 - \frac{S(B_1, TI_4)}{S_0}\right) \\ \vdots \end{pmatrix},$$

$$A = \begin{pmatrix} W_1 & W_1 \\ W_2 & W_2 \cdot \frac{TI_2}{TI_1} \\ W_3 & W_3 \cdot \frac{TI_3}{TI_1} \\ W_4 & W_4 \cdot \frac{TI_4}{TI_1} \\ \vdots & \end{pmatrix},$$

$$X = \begin{pmatrix} \log(1 - \cos(B_1 \cdot \alpha)) \\ -\frac{TI_1}{T_1} \end{pmatrix}$$

Here, S is a matrix of 1×n, A is a matrix of 2×n, and X is a matrix of 1×2. Wi (i=1, 2, 3, ..., n) indicates a weight for each TI, and can be arbitrarily set. By multiplying the pseudo-inverse matrix pinvA of the matrix A from the left, Expression (19) can be solved. As a result, B1 and T1 can be calculated as shown in the following Expressions (20) and (21).

[Expression 1]

$$B_1 = \frac{a\cos[1 - \exp[(pinvA)_{1i} S_i]]}{\alpha} \quad (20)$$

$$T_1 = \frac{TI_1}{(pinvA)_{2i} S_i} \quad (21)$$

In the first and second embodiments, the solution (B1) is calculated by solving Expressions (4) to (6) or the simultaneous equations of Expressions (13) and (14). Accordingly, in order for the solution not to diverge, the TI ratio of the signal acquisition sequences after pre-pulse is set as the integer ratio. In the present embodiment, however, since it is possible to find a solution without requiring such TI limitation, the effect of pre-pulse is high. In addition, since a signal can be acquired in a short TI, it is possible to reduce the measurement time and also to obtain the high-accuracy B1 distribution. In addition, in the present embodiment, it is possible to calculate not only the B1 distribution but also the T1 distribution. For example, as disclosed in NPL 4, the calculated T1 distribution is used for clinical diagnosis of osteoarthritis and the like.

Figure 10:
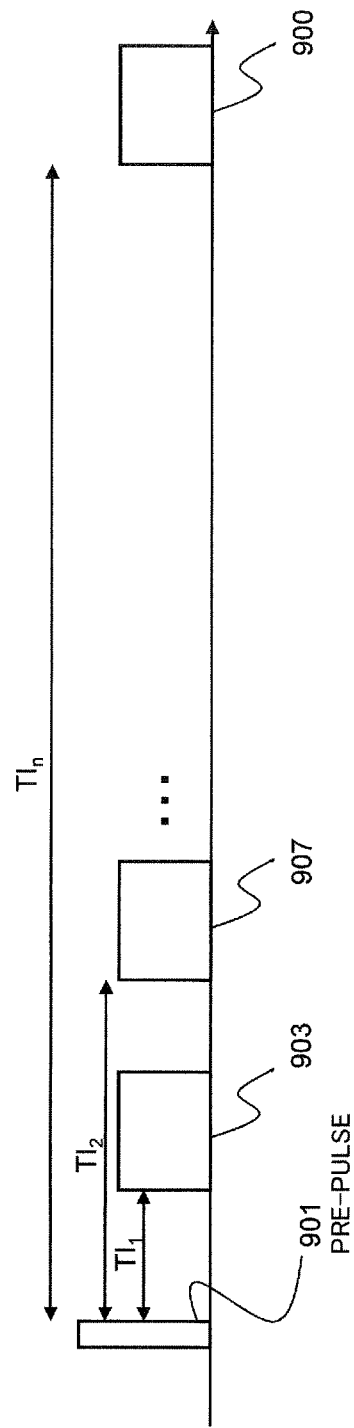
FIG. 10 is a diagram showing a modification of the third embodiment.

In addition, although the case where the reference image acquisition sequence 900 is executed immediately before the pre-pulse 901 to acquire the reference image has been described in FIG. 9, it is also possible to execute the reference signal acquisition sequence 900 after the passage of sufficient time, that is, sufficient time for T1 relaxation after the application of the pre-pulse 901. FIG. 10 shows this modification. As shown in FIG. 10, images of different TI are acquired by executing the signal acquisition sequences 903, 905, and 907 with different TI after the application of the pre-pulse 901, and sufficiently long TI is finally set and the reference image acquisition sequence 900 is executed to acquire the reference image. Since the signal intensity S0 of the reference image can be expressed as S0=Sseq as shown in Expression (17), the B1 distribution and the T1 distribution can be calculated by Expressions (18) to (21) in the same manner as in the case shown in FIG. 9.

Fourth Embodiment

The present embodiment is characterized in that the B1 distribution of a plurality of cross-sections is measured using a multi-slice method. Since others are the same as those in the first to third embodiments, explanation will be focused on the differences.

Figure 11:
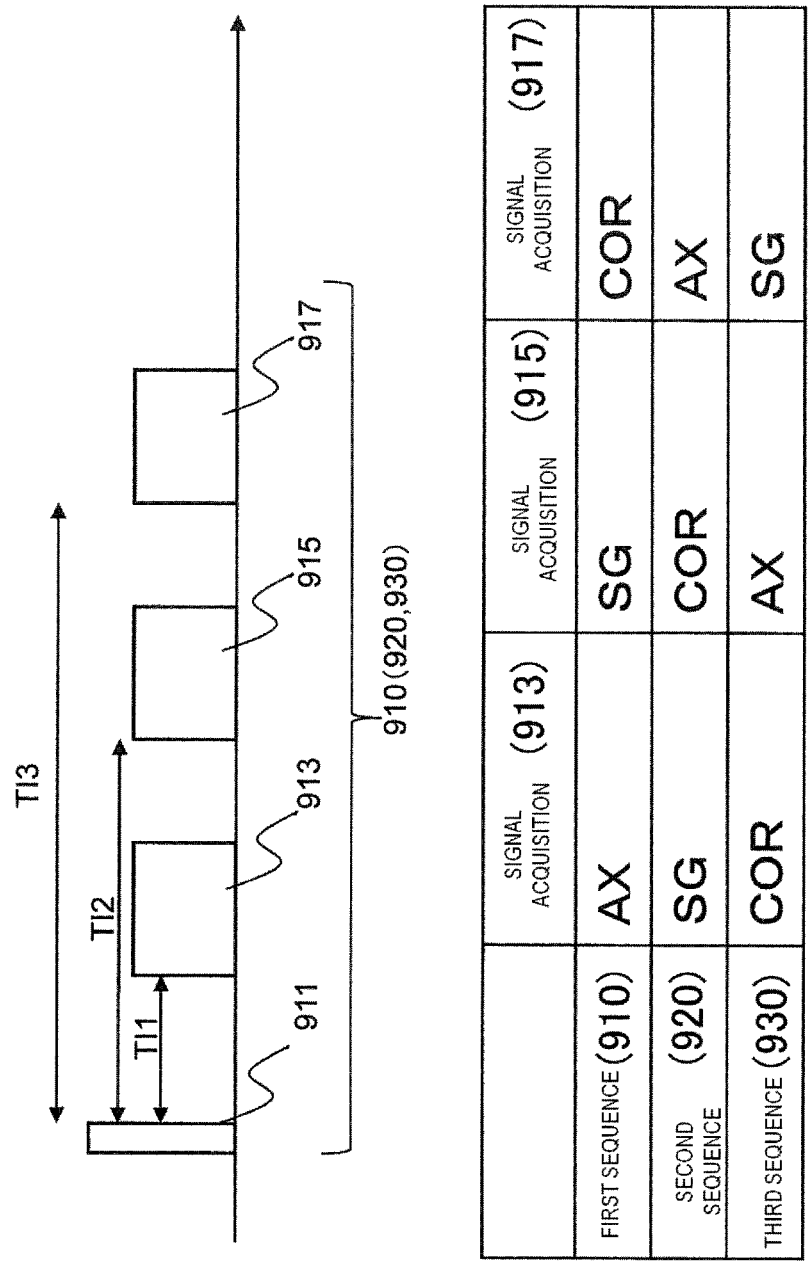
FIG. 11 is a diagram showing a fourth embodiment of the B1 distribution measurement sequence.

FIG. 11 shows an example of the B1 distribution measurement sequence according to the present embodiment. As shown in FIG. 11, the B1 distribution measurement sequence 910 is configured to include a pre-pulse 911 and signal acquisition sequences 913, 915, and 917 subsequent to the pre-pulse 911. Although the B1 distribution measurement sequence 910 is similar to the B1 distribution measurement sequence shown in FIG. 3, each of the signal acquisition sequences 913, 915, and 917 is executed on a cross-section selected from three cross-sections perpendicular to each other.

That is, for example, in the sequence shown in FIG. 4, the slice selection gradient magnetic field 402 applied simultaneously with the RF pulse 401 is a slice gradient magnetic field having a different axis for each signal acquisition sequence, and different cross-sections are excited. Accordingly, the image of each cross-section has different elapsed time TI from the application of the pre-pulse 911. The same B1 distribution measurement sequences 920 and 930 are repeated at predetermined intervals (TD). In this case, the order of slices (cross-sections) selected in the signal acquisition sequence included in each B1 distribution measurement sequence is cyclically changed. For example, the order in the first B1 distribution measurement sequence 910 is axial plane (AX), sagittal plane (SG), and coronal plane (COR), the order in the next B1 distribution measurement sequence 920 is SG→COR→AX, and the order in the next B1 distribution measurement sequence 930 is COR→AX→SG. Then, when the third B1 distribution measurement sequence 930 ends, three pieces of image data (k-space data of TI1, TI2, and TI3) of different TI can be obtained for each of the axial plane (AX), the sagittal plane (SG), and the coronal plane (COR).

FIG. 9 has shown the case where a plurality of cross-sections are three cross-sections perpendicular to each other. However, also when the plurality of cross-sections are parallel cross-sections, three or more sets of image data can be obtained for the plurality of parallel cross-sections by changing the slice selection conditions in each signal acquisition sequence, in the same manner as the case of three cross-sections perpendicular to each other.

Then, calculating the B1 distribution by Expressions (1) to (9) using these three sets of data is the same as that in the first embodiment.

Instead of the B1 distribution measurement sequence shown in FIG. 9, the B1 distribution measurement sequence shown in FIG. 7(a) or 7(b) is also possible. Also in this case, similar to the second embodiment, it is possible to calculate the B1 distribution for each cross-section using Expressions (10) to (15).

In addition, by acquiring a reference image without applying the pre-pulse, it is possible to calculate the B1 distribution using Expressions (18) to (21) as in the third embodiment.

The present embodiment is effective for RF shimming for which the B1 distribution of a plurality of cross-sections is required. According to the present embodiment, compared with the first to third embodiments, the measurement time increases in proportion to the number of cross-sections. However, since the measurement time of one B1 distribution measurement sequence is only about several seconds, it is possible to calculate the B1 distribution in a short time of about 10 to 30 seconds for three cross-sections.

Fifth Embodiment

In the present embodiment, k-space data used for the calculation of the B1 distribution is measured multiple times. That is, the present embodiment is characterized in that multi-shot measurement is performed. Since others are the same as those in the first to third embodiments, explanation will be focused on the differences.

Figure 12:
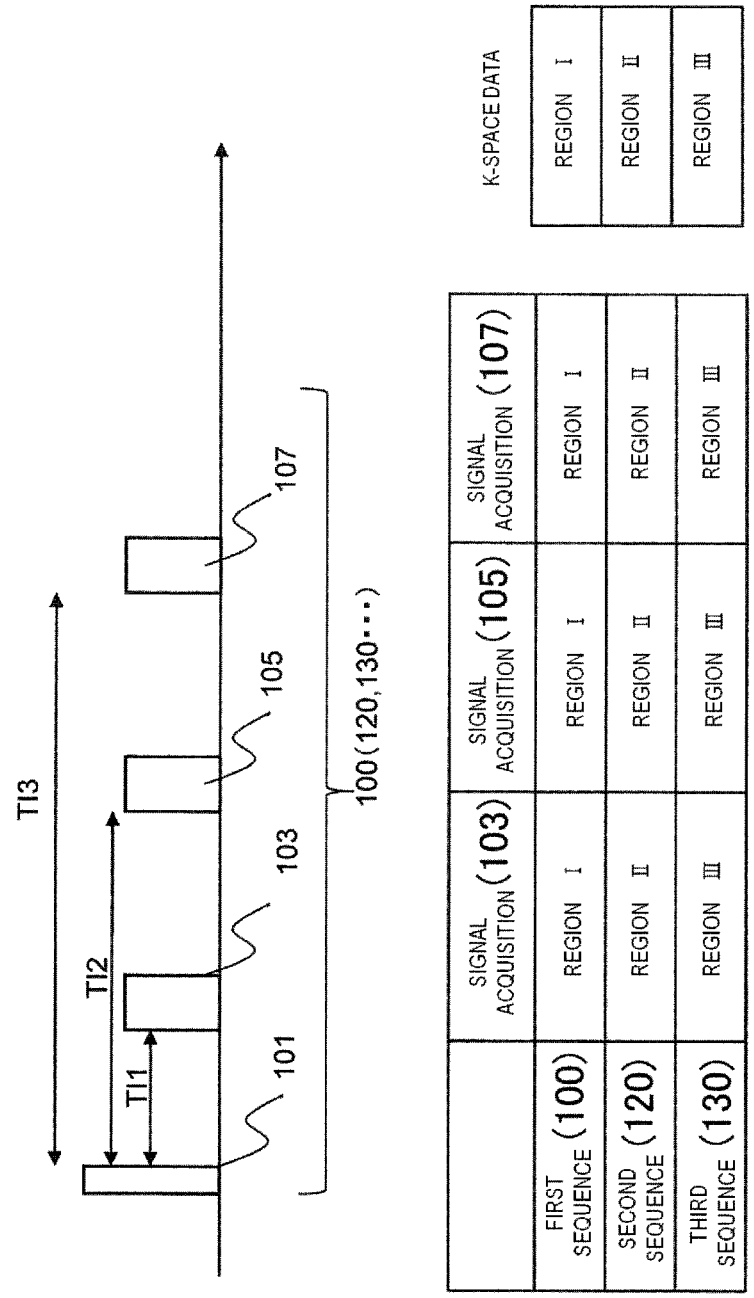
FIG. 12 is a diagram showing a fifth embodiment of the B1 distribution measurement sequence.

In the present embodiment, as shown in FIG. 12, a B1 distribution measurement sequence 100 configured to include a pre-pulse 101 and a plurality of signal acquisition sequences 103, 105, and 107 is performed multiple times. Although the pre-pulse 101 of the same flip angle is used in each sequence, a part of k-space data is acquired in one signal acquisition sequence and all pieces of the k-space data are acquired in multiple sequences. The method for dividing k-space is not particularly limited, and k-space may be simply divided into a plurality of regions as shown in the drawing, or it is also possible to perform measurement by making the phase encoding step loose in each of the signal acquisition sequence 110, 120, 130, . . . and to measure the data closest to the center of k-space always in predetermined TI.

In the first to third embodiments, the case has been described in which the timing to acquire the central data when acquiring all pieces of k-space data in one sequence is set to predetermined TI (elapsed time from pre-pulse application). In this case, however, data of different TI is included in the k-space data. In the present embodiment, since the k-space data is separately acquired, the rate of data which is included in the k-space data and whose TI is different from predetermined TI can be reduced. As a result, the signal acquisition time is increased several times the number of shots, but it is possible to improve the accuracy of B1 distribution measurement.

Figure 6:
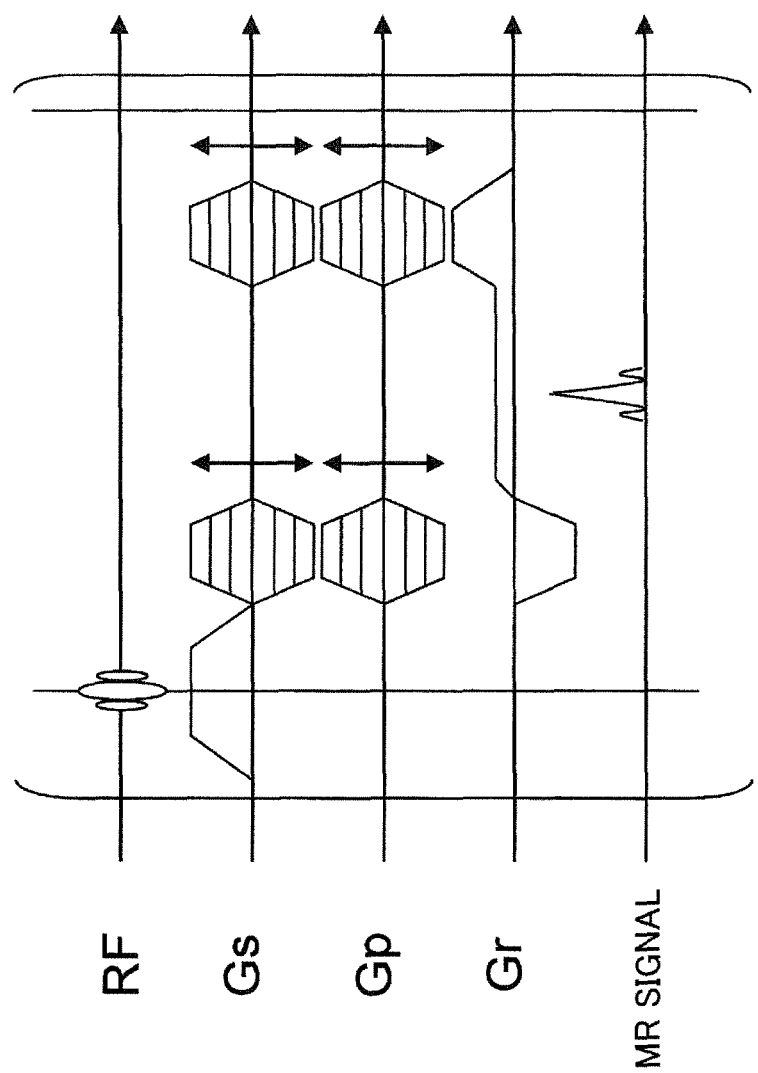
FIG. 6 is a timing chart showing still another example of the signal acquisition sequence.

The present embodiment is particularly effective when the radial sequence shown in FIG. 5 or the 3D pulse sequence shown in FIG. 6 is adopted as a signal acquisition sequence.

Sixth Embodiment

Although the case where a plurality of signal acquisition sequences having different TI are executed continuously after one pre-pulse has been described in the first and second embodiment, the present embodiment is characterized in that a plurality of pieces of image data of different TI are obtained by performing one signal acquisition sequence after one pre-pulse and repeating the B1 distribution measurement sequence, which is configured to include the one pre-pulse and one signal acquisition sequence, while changing the TI of the signal acquisition sequence.

Figure 13:
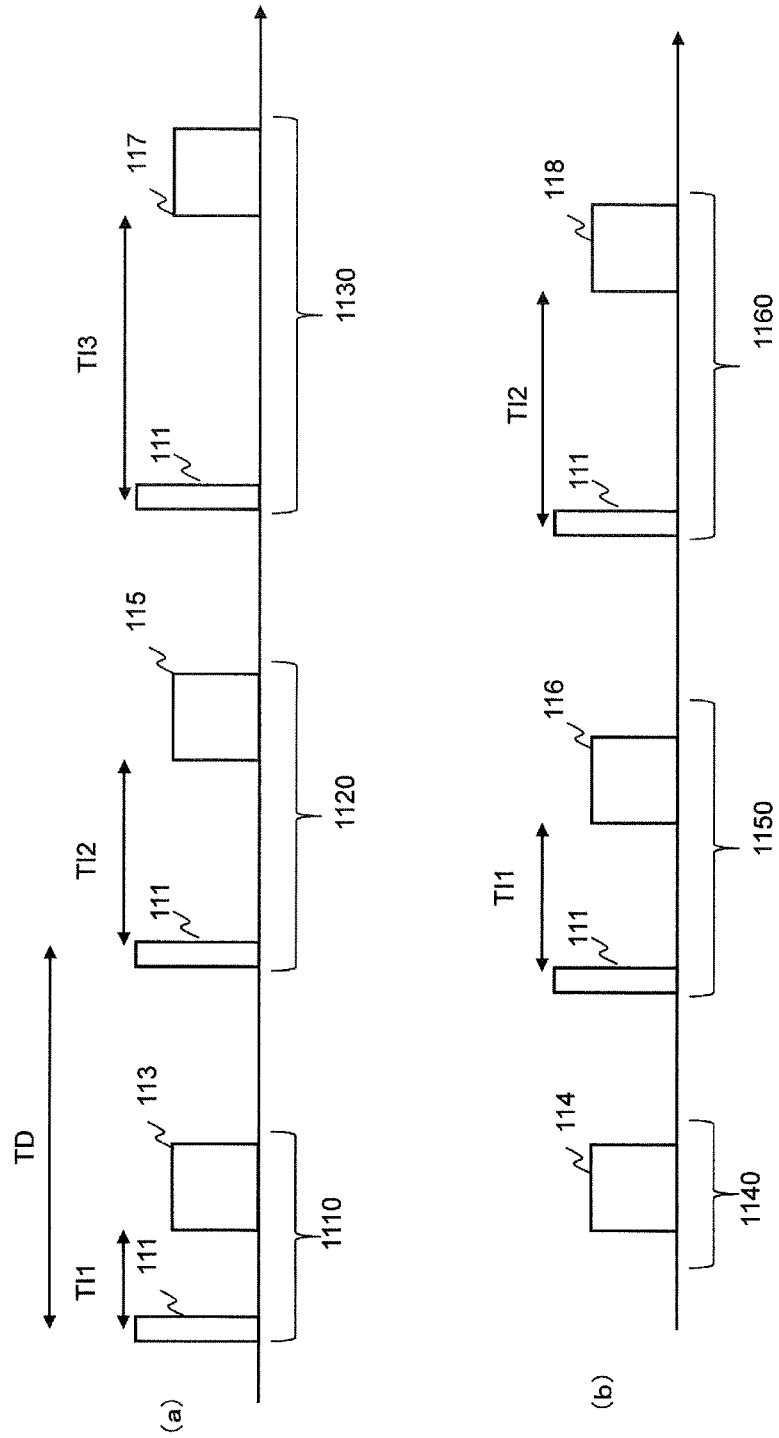
FIGS. 13($a$) and 13($b$) are diagrams showing a sixth embodiment of the B1 distribution measurement sequence.

FIG. 13 shows the B1 distribution measurement sequence of the present embodiment. FIG. 13(a) shows a case where the B1 distribution measurement sequence of the first embodiment is changed according to the present embodiment, FIG. 13(b) shows a case where the B1 distribution measurement sequence of the second embodiment is changed according to the present embodiment. In FIG. 13(a), a pre-pulse 111 and signal acquisition sequences 113, 115, and 117 used in three B1 distribution measurement sequences 1110, 1120, and 1130 are the same in all of the three sequences, but only TI is different. In addition, in FIG. 13(b), signal acquisition sequences 114, 116, and 118 used in three B1 distribution measurement sequences 1140, 1150, and 1160 are the same, but no pre-pulse is used in the first B1 distribution measurement sequence 1140 (equivalent to the flip angle 0). In addition, only TI is different between the second B1 distribution measurement sequence 1150 and the third B1 distribution measurement sequence 1160.

As described above, the RF pulse used in the signal acquisition sequence is a small flip angle pulse having a flip angle of 10° or less. However, when signal acquisition sequences are continuously executed, subsequent signal acquisition sequences are influenced by the RF pulse applied in the preceding signal acquisition sequence. In the present embodiment, since the signal acquisition sequences having different TI are executed separately, image data that accurately reflects the TI can be obtained without being influenced by respective RE pulses. In addition, since the number of repetitions of the B1 distribution measurement sequence is about 3, an increase in measurement time due to repetition is small. Accordingly, in both cases of FIGS. 13(a) and 13(b), the collection of data required for the B1 distribution can be completed in about 15 seconds.

Until now, typical embodiments of the B1 measurement step 202 and the B1 distribution calculation step 203 performed for each channel of the coil among the operations of the MRI apparatus of the present invention shown in FIG. 2 have been described. However, these embodiments may be appropriately combined, and neither the pulse sequence nor the number of repetitions is limited to those illustrated and various changes may be made.

<<Setting of the Amplitude and Phase of RF Pulse (Steps 204 and 205)>>

Next, RF pulse adjustment (steps 204 and 205 in FIG. 2) using the B1 distribution calculated in step 203 will be described. Here, a case will be described in which the RF coil is a multiple array coil formed by a plurality of small RF coils and a feeding point (channel), which can be independently controlled, is set for each of the small RF coils.

Assuming that the number of channels of the RF coil is N, the B1 distribution calculated for each channel is B1n(r), and the amplitude and phase of a high-frequency signal supplied to each small RF coil is An and φn, the magnetic field distribution $B1_{total}(r)$ as a whole can be expressed as in Expression (22).

$$B1_{total}(r) = \Sigma A_n \exp(i\phi_n) B1_n(r) \quad (22)$$

By changing the set (An, φn) of amplitude and phase in Expression (22), a set of amplitude and phase to give a uniform magnetic field distribution B1 (r) is calculated as the magnetic field distribution $B1_{total}(r)$ (r is the position of the real space coordinate). This calculation can be solved using a known nonlinear optimization algorithm. For example, the set (An, φn) of amplitude and phase can be calculated using an optimization algorithm that minimizes the square root of the mean square error of $B1_{total}(r)$ calculated in Expression (22) and the target magnetic field distribution.

The calculated set of amplitude and phase is set for each small RF coil. Specifically, the amplitude and timing of the high-frequency pulse supplied to each channel of the RF coil are adjusted by the sequencer 4 and the modulator 12.

Figure 14:
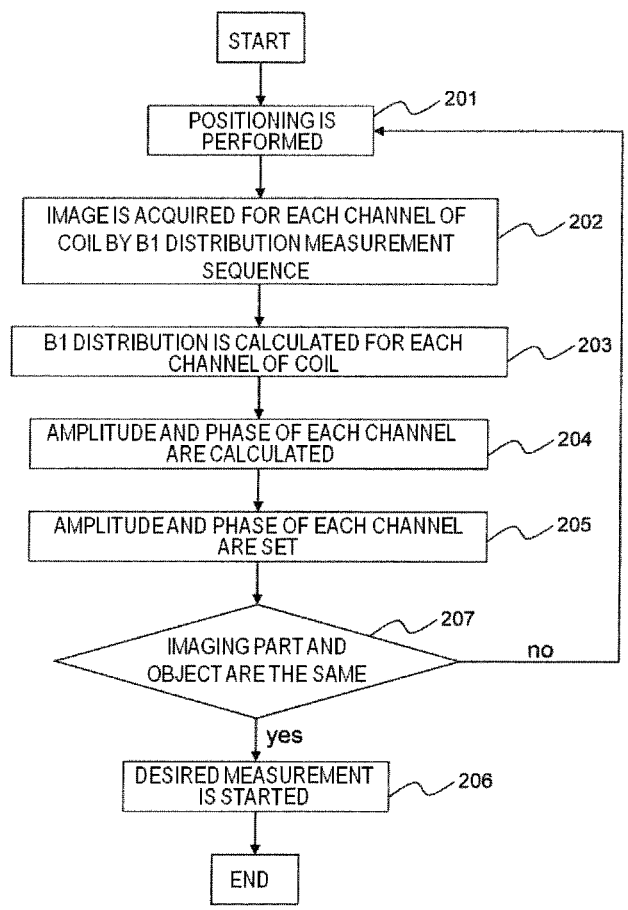
FIG. 14 is a flowchart showing another embodiment of the B1 distribution measurement procedure according to the present invention.

Desired imaging is performed using the amplitude and the phase set in steps 204 and 205 (step 206). In addition, the B1 distribution measured in step 202 depends on a measured part of the object. Therefore, when an object or an imaging part changes, it is preferable to perform re-measurement of the B1 distribution. FIG. 14 shows the procedure including a change of an object or an imaging part. In FIG. 14, the same steps as in FIG. 2 are denoted by the same reference numerals. In this flow, at the timing of change of an object or an imaging part (step 207), the process returns to step 201 to perform the measurement of the B1 distribution and the setting of the amplitude and phase of each small RF coil reflecting the measurement result. Thus, by measuring the B1 distribution only when the object or the imaging part changes, it is possible to reduce the number of times of B1 distribution measurement. As a result, it is possible to improve the throughput of the test.

In addition, although the case where the RF coil is a multiple array coil has been described in the above embodiment, the present invention may also be similarly applied to a case where a plurality of independent RF coils are used as an RF coil.

In addition, in the flows shown in FIGS. 2 and 14, the case where the B1 distribution is measured for each channel for the radiation coil having a plurality of channels. However, it is also possible to acquire the B1 distribution by combining two or more channels. For example, in the case of a 4-channel radiation coil, image acquisition is performed four times while changing the combination of three channels. Then, a B1 distribution based on the combination of B1 distributions of three channels is calculated by Expression (5). For example, B1 distributions (B11 to B14) obtained by four B1 distribution measurements are expressed as in the following Expressions (23) to (26).

$$B11 = B1a + B1b + B1c \quad (23)$$

$$B12 = B1b + B1c + B1d \quad (24)$$

$$B13 = B1a + B1c + B1d \quad (25)$$

$$B14 = B1a + B1b + B1d \quad (26)$$

Therefore, from these Expressions, B1a to B1d of the respective channels can be calculated by the following Expressions (27) to (30).

$$B1a = \{(B11 + B13 + B14) - 2B12\}/3 \quad (27)$$

$$B1b = \{(B11 + B12 + B14) - 2B13\}/3 \quad (28)$$

$$B1c = \{(B11 + B12 + B13) - 2B14\}/3 \quad (29)$$

$$B1d = \{(B12 + B13 + B14) - 2B11\}/3 \quad (30)$$

Step 204 after calculating the B1 distribution of each channel is the same as described above.

In addition, when performing RF shimming using only two channels, two channels to be used may be combined to acquire an image.

In addition, although the case of adjusting the phase and amplitude of the RF coil using the result of B1 distribution measurement has been described in the above embodiments, one of the features of the present invention is that it is an MRI apparatus having a method of B1 distribution measurement, that is, a specific B1 distribution measurement sequence, and it is also possible to correct the data collected by the imaging sequence using the B1 distribution instead of adjusting the phase and amplitude of the RF coil using the measured B1 distribution. In this case, the present invention may also be applied to a single RF coil.

In addition, the calculated B1 distribution may also be used to correct error of T2 values due to non-uniform B1, as post-processing when acquiring the T2 distribution, instead of being used for RF shimming. T2 value correction using the B1 distribution is disclosed in NPL 5, for example.

The features of the present invention that has been apparent from the explanation of each of the above embodiments can be summarized as follows.

That is, an MRI apparatus of the present invention includes: an RF radiation unit that radiates a high-frequency magnetic field (B1) to cause nuclear magnetic resonance in an object; an imaging unit that images the object using a B1 distribution measurement sequence that includes a signal acquisition sequence to acquire a nuclear magnetic resonance signal by setting elapsed time (TI) from application of a high-frequency magnetic field pre-pulse; and a calculation unit that reconstructs an image of the object using the nuclear magnetic resonance signal and is characterized in that the calculation unit calculates an irradiation magnetic field distribution of the RF radiation unit using the image and the calculation unit calculates the irradiation magnetic field distribution using a plurality of images with the different elapsed time.

Preferably, the B1 distribution measurement sequence includes a plurality of signal acquisition sequences with the different elapsed time, and the calculation unit reconstructs the plurality of images with the different elapsed time using nuclear magnetic resonance signals acquired in the plurality of signal acquisition sequences with the different elapsed time.

In addition, preferably, the imaging unit acquires images by executing a plurality of B1 distribution measurement sequences in which application conditions of the high-frequency magnetic field pre-pulse are different, and the calculation unit calculates the irradiation magnetic field distribution using images acquired in the plurality of B1 distribution measurement sequences in which the application conditions of the high-frequency magnetic field pre-pulse are different.

In addition, preferably, among the plurality of B1 distribution measurement sequences, a first B1 distribution measurement sequence is a signal acquisition sequence executed without using the high-frequency magnetic field pre-pulse, and a second B1 distribution measurement sequence includes an application of the high-frequency magnetic field pre-pulse and at least two signal acquisition sequences subsequent to the application of the high-frequency magnetic field pre-pulse.

In addition, preferably, the calculation unit calculates the irradiation magnetic field distribution by solving a determinant using a ratio between a signal intensity of an image, which is obtained by reconstructing a nuclear magnetic resonance signal acquired in a signal acquisition sequence of the first B1 distribution measurement sequence, and each signal intensity of a plurality of images, which are obtained by reconstructing nuclear magnetic resonance signals acquired in a plurality of signal acquisition sequences of the second B1 distribution measurement sequence.

In addition, preferably, the imaging unit executes the B1 distribution measurement sequence for each of a plurality of cross-sections, and the calculation unit calculates the irradiation magnetic field distribution for each of the plurality of cross-sections.

In addition, preferably, the signal acquisition sequence is a multi-slice imaging sequence or a three-dimensional imaging sequence.

In addition, preferably, the imaging unit includes a plurality of the B1 distribution measurement sequences in which application conditions of the high-frequency magnetic field pre-pulse are the same, and separately acquires all pieces of data required to reconstruct the images in the plurality of B1 distribution measurement sequences.

In addition, preferably, the imaging unit executes the B1 distribution measurement sequence multiple times while changing the elapsed time, and the calculation unit reconstructs the plurality of images with the different elapsed time using nuclear magnetic resonance signals acquired in the respective B1 distribution measurement sequences.

In addition, preferably, the high-frequency magnetic field pre-pulse is a high-frequency magnetic field pulse having a flip angle of 90° or more.

In addition, preferably, in the signal acquisition sequence, a high-frequency magnetic field pulse having a flip angle of 10° or less is repeatedly applied to acquire the nuclear magnetic resonance signal.

In addition, preferably, in the imaging unit, the plurality of signal acquisition sequences are continuous, and the high-frequency magnetic field pulse is applied at a fixed repetition time.

In addition, preferably, the signal acquisition sequence includes an application of a high-frequency magnetic field pulse without acquisition of a nuclear magnetic resonance signal.

In addition, preferably, the calculation unit calculates the irradiation magnetic field distribution by solving simultaneous equations using signal intensities of the plurality of images with the different elapsed time.

In addition, preferably, the signal acquisition sequence is a pulse sequence to acquire the nuclear magnetic resonance signal by scanning k-space radially.

In addition, preferably, the calculation unit adjusts at least one of phase and amplitude of a high-frequency magnetic field, which is supplied to the RF radiation unit, on the basis of the calculated irradiation magnetic field distribution.

In addition, preferably, the RF radiation unit has a plurality of channels, the imaging unit images the object by executing the B1 distribution measurement sequence for each of the channels, and the calculation unit calculates the irradiation magnetic field distribution for each of the channels.

In addition, an irradiation magnetic field measuring method of the present invention is a method for measuring the irradiation magnetic field distribution of an RF radiation unit in a magnetic resonance imaging apparatus including the RF radiation unit, and includes: a measurement step of executing a signal acquisition sequence to acquire a nuclear magnetic resonance signal by setting elapsed time (TI) from application of a high-frequency magnetic field pre-pulse by the RF radiation unit; an image reconstruction step of reconstructing an image of the object using the nuclear magnetic resonance signal; and an irradiation magnetic field distribution calculation step of calculating the irradiation magnetic field distribution of the RF radiation unit using the image and is characterized in that, in the irradiation magnetic field distribution calculation step, the irradiation magnetic field distribution is calculated using a plurality of images with the different elapsed time.

Preferably, in the measurement step, a plurality of signal acquisition sequences with the different elapsed time from application of the high-frequency magnetic field pre-pulse are executed. In the image reconstruction step, the plurality of images with the different elapsed time are reconstructed using nuclear magnetic resonance signals acquired in the plurality of signal acquisition sequences with the different elapsed time.

In addition, preferably, the measurement step includes a step of executing only a signal acquisition sequence without using the high-frequency magnetic field pre-pulse and a step of executing an application of the high-frequency magnetic field pre-pulse and at least two signal acquisition sequences subsequent to the application of the high-frequency magnetic field pre-pulse. In the irradiation magnetic field distribution calculation step, the irradiation magnetic field distribution is calculated by solving a determinant using a ratio of signal intensities of a plurality of images that are obtained by reconstructing nuclear magnetic resonance signals acquired in the signal acquisition sequences.

First Example

Using the B1 distribution measurement sequence shown in FIG. 13(a), three pieces of image data of different TI were obtained with the following parameters. The imaging time was 15 seconds.
Pre-pulse: flip angle 90°
TR: 5000 ms
The number of phase encoding: 64

TI: 150 ms, 300 ms, 450 ms

Figure 15:
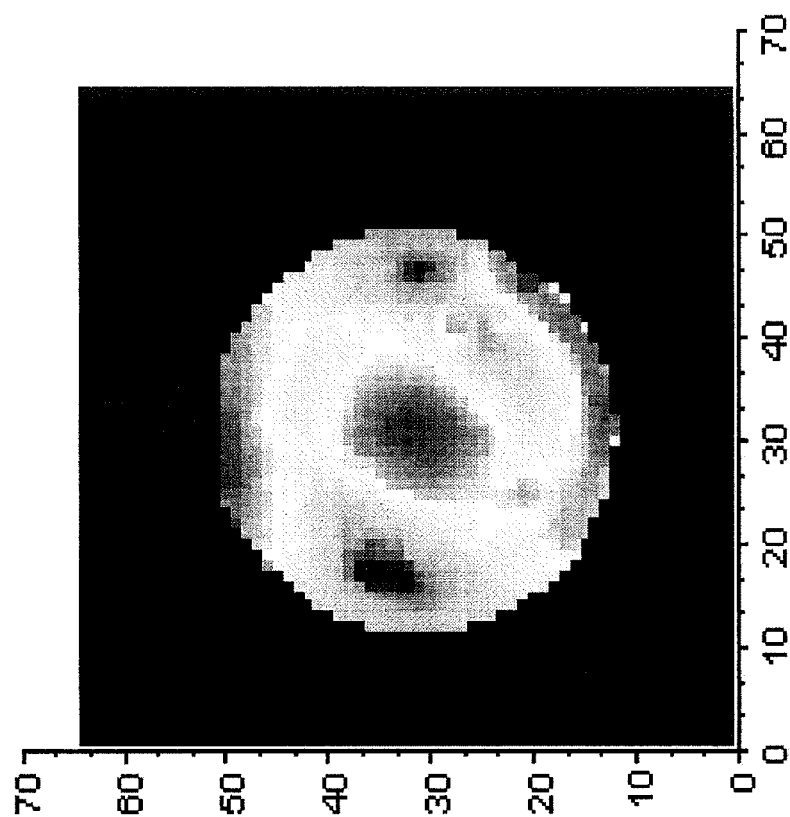
FIG. 15 is a diagram showing the result of B1 distribution calculation in a first example.

The result of B1 distribution calculation using these pieces of image data is shown in FIG. 15.

Second Example

Figure 16:
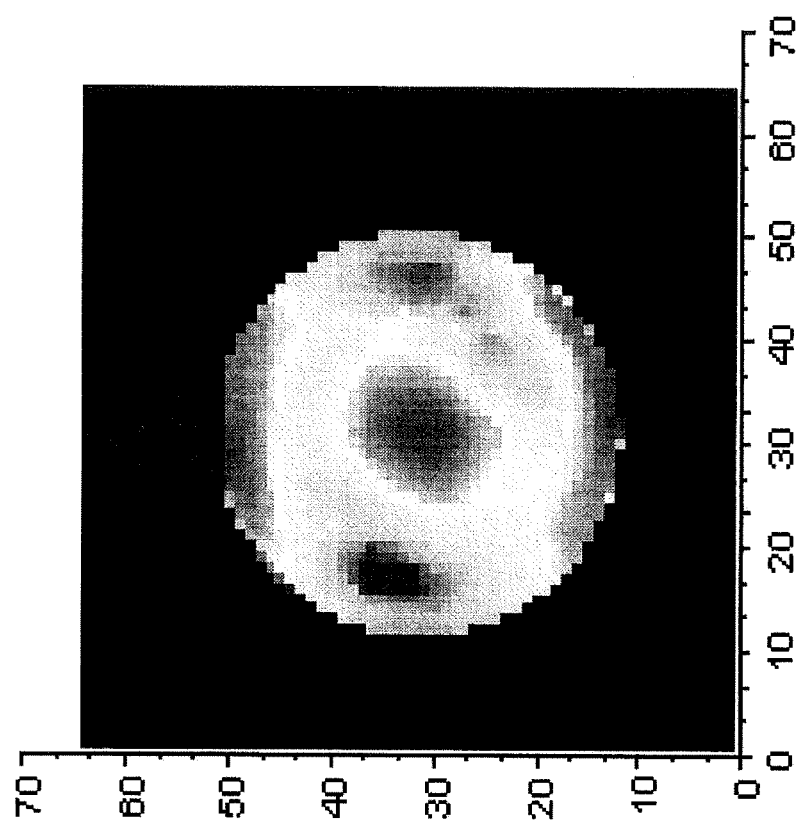
FIG. 16 is a diagram showing the result of B1 distribution calculation in a second example.

Using the B1 distribution measurement sequence shown in FIG. 13(b), three pieces of image data of different TI were obtained with the same parameters as in the first example. The imaging time was 15 seconds. The result of B1 distribution calculation using these pieces of image data is shown in FIG. 16.

Figure 17:
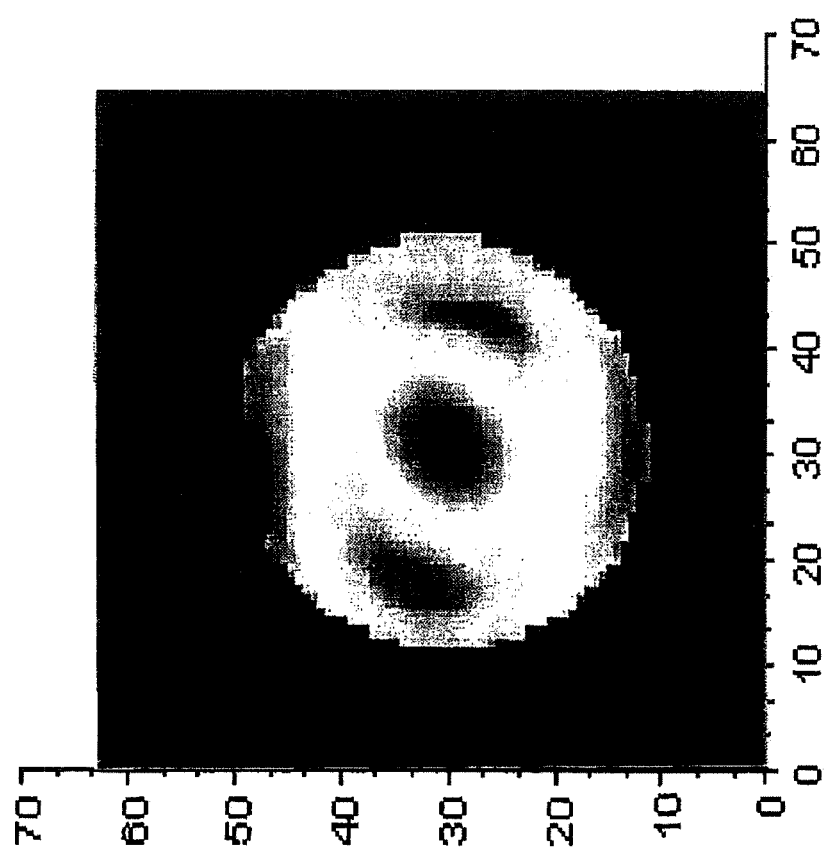
FIG. 17 is a diagram showing the result of B1 distribution calculation in a conventional method (DAM).

The results (FIGS. 15 and 16) obtained in these examples were the same accuracy as in the result (FIG. 17) obtained in the conventional method (Double Angle method).

Third Example

Figure 18:
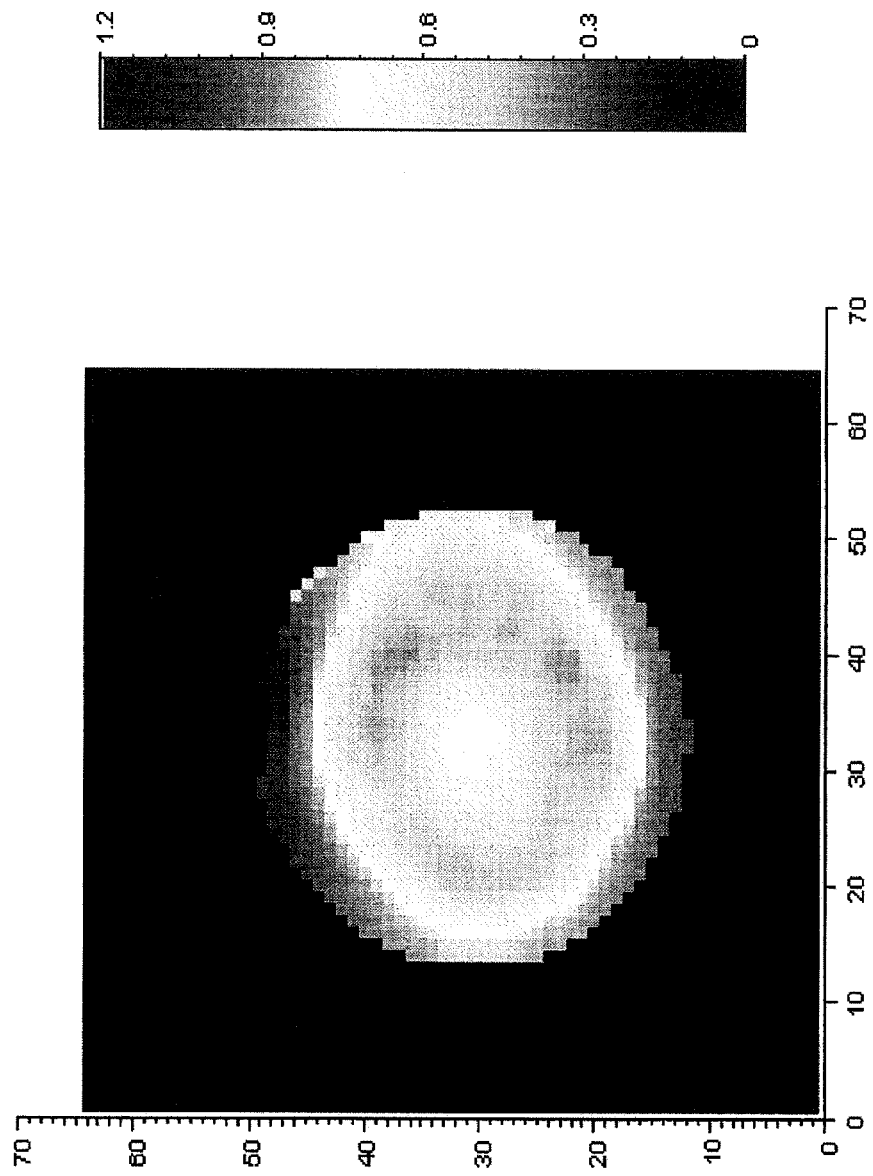
FIG. 18 is a diagram showing the result of B1 distribution calculation in a third example.

Using the B1 distribution measurement sequence shown in FIG. 9, three pieces of image data including one reference image were obtained under the conditions in which TR and the number of phase encoding were the same as those in the first example, TI1=50 ms, and TI2=150 ms. The imaging time was about 500 ms. When the number of encoding is reduced from 64 to 32, the imaging time can be further reduced to 350 ms. The result when the calculation of B1 distribution using the same calculation method as in the third embodiment was performed using these pieces of image data is shown in FIG. 18.

Figure 19:
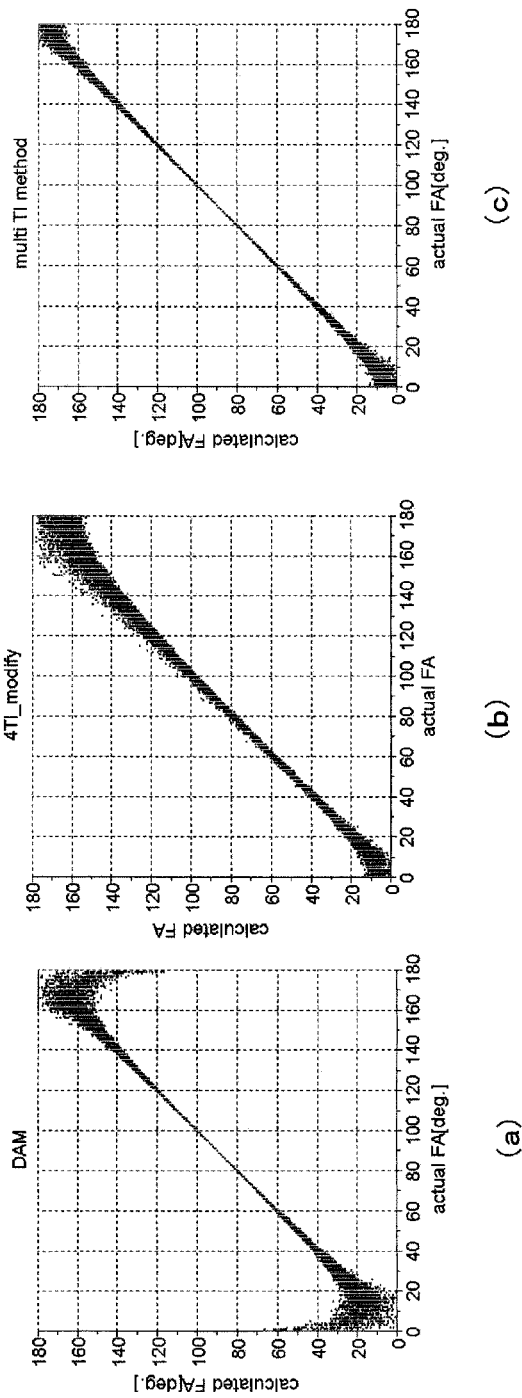
FIG. 19 is a diagram showing the comparison result of the calculation accuracy of the method of the present invention and the calculation accuracy of the conventional method (DAM).

The comparison result of the calculation accuracy of the method of the present invention and the calculation accuracy of the conventional method (DAM) is shown in FIG. 19. In FIG. 19, (a) shows the DAM, (b) shows the first example, and (c) shows the third example. In FIG. 19, the horizontal axis indicates an actual flip angle set for the transmission coil, and the vertical axis indicates a flip angle calculated by each method and also calculated from B1. If there is no error of calculation, the value on the horizontal axis is the same as the value on the vertical axis, resulting in a graph of y=x. It can be seen that the B1 distribution can be calculated most accurately using the method of the third example.

In addition, in the case of measurement using the same imaging parameter, the imaging time was 10.8 minutes in the DAM, but the imaging time could be significantly reduced to 15 seconds in the first and second examples and could be further reduced to 500 ms in the third example.

INDUSTRIAL APPLICABILITY

According to the present invention, conventional RF pulse magnetic field distribution measurement (B1 measurement) can be performed in a very short time. Therefore, since the B1 measurement and RF pulse control based on the measurement result can be performed in real time according to a change of an imaging part, the burden on the object due to an increase in imaging time can be reduced. In addition, in a high magnetic field MRI that is easily influenced by the magnetic field in the body of the object, an image of high diagnostic performance can be provided by eliminating the influence.

REFERENCE SIGNS LIST

2: static magnetic field generation system
3: gradient magnetic field generation system
4: sequencer
5: signal transmission system
6: signal receiving system
7: signal processing system
8: CPU
11: high-frequency oscillator
12: modulator
13: amplifier
14a: high-frequency coil (transmission coil)

The invention claimed is:

1. A magnetic resonance imaging apparatus comprising:
an RF radiation unit that radiates a high-frequency magnetic field (B1) to cause nuclear magnetic resonance in an object;
an imaging unit that images the object using a B1 distribution measurement sequence that includes a signal acquisition sequence to acquire a nuclear magnetic resonance signal with elapsed time (TI) between (a) application of a high-frequency magnetic field pre-pulse and (b) application of the signal acquisition sequence; and
a calculation unit that reconstructs an image of the object using the nuclear magnetic resonance signal,
wherein the calculation unit calculates an irradiation magnetic field distribution of the RF radiation unit using a plurality of images with the different elapsed time.

2. The magnetic resonance imaging apparatus according to claim 1,
wherein the imaging unit acquires images by executing a plurality of B1 distribution measurement sequences in which application conditions of the high-frequency magnetic field pre-pulse are different, and
the calculation unit calculates the irradiation magnetic field distribution using images acquired in the plurality of B1 distribution measurement sequences in which the application conditions of the high-frequency magnetic field pre-pulse are different.

3. The magnetic resonance imaging apparatus according to claim 2,
wherein among the plurality of B1 distribution measurement sequences, a first B1 distribution measurement sequence is a signal acquisition sequence executed without using the high-frequency magnetic field pre-pulse, and a second B1 distribution measurement sequence includes an application of the high-frequency magnetic field pre-pulse and at least two signal acquisition sequences subsequent to the application of the high-frequency magnetic field pre-pulse.

4. The magnetic resonance imaging apparatus according to claim 3,
wherein the calculation unit calculates the irradiation magnetic field distribution by solving a determinant using a ratio between the signal intensity of an image, which is obtained by reconstructing a nuclear magnetic resonance signal acquired in a signal acquisition sequence of the first B1 distribution measurement sequence, and each signal intensity of a plurality of images, which are obtained by reconstructing nuclear magnetic resonance signals acquired in a plurality of signal acquisition sequences of the second B1 distribution measurement sequence.

5. The magnetic resonance imaging apparatus according to claim 1,
wherein the imaging unit executes the B1 distribution measurement sequence for each of a plurality of cross-sections, and
the calculation unit calculates the irradiation magnetic field distribution for each of the plurality of cross-sections.

6. The magnetic resonance imaging apparatus according to claim 5, wherein the signal acquisition sequence is a multi-slice imaging sequence or a three-dimensional imaging sequence.

7. The magnetic resonance imaging apparatus according to claim 1,
wherein the imaging unit includes a plurality of the B1 distribution measurement sequences in which application conditions of the high-frequency magnetic field pre-pulse are the same, and separately acquires all pieces of data required to reconstruct the images in the plurality of B1 distribution measurement sequences.

8. The magnetic resonance imaging apparatus according to claim 1,
wherein the imaging unit executes the B1 distribution measurement sequence multiple times while changing the elapsed time, and
the calculation unit reconstructs the plurality of images with the different elapsed time using nuclear magnetic resonance signals acquired in the respective B1 distribution measurement sequences.

9. The magnetic resonance imaging apparatus according to claim 1,
wherein the high-frequency magnetic field pre-pulse is a high-frequency magnetic field pulse having a flip angle of 90° or more.

10. The magnetic resonance imaging apparatus according to claim 1,
wherein the signal acquisition sequence is a pulse sequence to acquire the nuclear magnetic resonance signal by scanning k-space radially.

11. The magnetic resonance imaging apparatus according to claim 1,
wherein the RF radiation unit has a plurality of channels,
the imaging unit images the object by executing the B1 distribution measurement sequence for each of the channels, and
the calculation unit calculates the irradiation magnetic field distribution for each of the channels.

12. A magnetic resonance imaging apparatus comprising:
an RF radiation unit that radiates a high-frequency magnetic field (B1) to cause nuclear magnetic resonance in an object;
an imaging unit that images the object using a B1 distribution measurement sequence includes a plurality of signal acquisition sequences, to acquire a nuclear magnetic resonance signal, with elapsed time (TI) between application of a high-frequency magnetic field pre-pulse and each of the plurality of signal acquisition sequences with the different elapsed time, and
a calculation unit that reconstructs a plurality of images with the different elapsed time of the object using the nuclear magnetic resonance signals acquired in the plurality of signal acquisition sequences with the different elapsed time,
wherein the calculation unit calculates an irradiation magnetic field distribution of the RF radiation unit using a plurality of images with the different elapsed time.

13. The magnetic resonance imaging apparatus according to claim 12,
wherein, in the signal acquisition sequence, a high-frequency magnetic field pulse having a flip angle of 10° or less is repeatedly applied to acquire the nuclear magnetic resonance signal.

14. The magnetic resonance imaging apparatus according to claim 13,
wherein, in the imaging unit, the plurality of signal acquisition sequences are continuous, and the high-frequency magnetic field pulse is applied at a fixed repetition time.

15. A method for measuring the irradiation magnetic field distribution of an RF radiation unit in a magnetic resonance imaging apparatus including an RF radiation unit, the irradiation magnetic field measuring method comprising:
a measurement step of executing a signal acquisition sequence to acquire a nuclear magnetic resonance signal by setting elapsed time (TI) from application of a high-frequency magnetic field pre-pulse by the RF radiation unit;
an image reconstruction step of reconstructing an image of the object using the nuclear magnetic resonance signal; and
an irradiation magnetic field distribution calculation step of calculating the irradiation magnetic field distribution of the RF radiation unit using the image,
wherein, in the irradiation magnetic field distribution calculation step, the irradiation magnetic field distribution is calculated using a plurality of images with the different elapsed time.

* * * * *